US011925563B2

(12) United States Patent
Mutchler et al.

(10) Patent No.: US 11,925,563 B2
(45) Date of Patent: Mar. 12, 2024

(54) MODULAR HUMERAL HEAD AND RELATED METHODS

(71) Applicant: HOWMEDICA OSTEONICS CORP., Mahwah, NJ (US)

(72) Inventors: Austin Wyatt Mutchler, Warsaw, IN (US); Kevin P. Knox, Fort Wayne, IN (US)

(73) Assignee: HOWMEDICA OSTEONICS CORP., Mahwah, NJ (US)

( * ) Notice: Subject to any disclaimer, the term of this patent is extended or adjusted under 35 U.S.C. 154(b) by 156 days.

(21) Appl. No.: 17/454,842

(22) Filed: Nov. 15, 2021

(65) Prior Publication Data

US 2022/0071771 A1 Mar. 10, 2022

Related U.S. Application Data

(62) Division of application No. 15/938,214, filed on Mar. 28, 2018, now Pat. No. 11,197,764.

(Continued)

(51) Int. Cl.
*A61F 2/30* (2006.01)
*A61F 2/40* (2006.01)
*A61F 2/38* (2006.01)

(52) U.S. Cl.
CPC .. *A61F 2/4014* (2013.01); *A61F 2002/30329* (2013.01); *A61F 2002/30332* (2013.01);
(Continued)

(58) Field of Classification Search
CPC .............. A61F 2002/30329; A61F 2/40; A61F 2002/30354; A61F 2/4014; A61F 2002/30617; A61F 2002/4037
See application file for complete search history.

(56) References Cited

U.S. PATENT DOCUMENTS 4,310,931 A 1/1982 Muller
5,314,479 A 5/1994 Rockwood, Jr. et al.
(Continued)

FOREIGN PATENT DOCUMENTS

DE 102008010478 8/2009
EP 1402854 3/2004
(Continued)

OTHER PUBLICATIONS

International Search Report and Written Opinion for PCT/US2018/024824 dated Jul. 10, 2018 in 12 pages.
(Continued)

*Primary Examiner* — Bruce E Snow
(74) *Attorney, Agent, or Firm* — DUANE MORRIS LLP

(57) ABSTRACT

Provided is a method of assembling an articular component of a prosthetic shoulder joint. The method includes: engaging an end of a coupler of a joint implant with a coupling portion of another component of the joint implant; providing relative rotation between the end of the coupler and the coupling portion of the other component of the joint implant along a continuous range of rotational positions while the end is engaged with the coupling portion of the other component of the joint implant; selecting an amount of eccentricity corresponding to a position within the continuous range of rotational position; and securing the other component of the joint implant to the end of the coupler at the selected amount of eccentricity.

13 Claims, 20 Drawing Sheets

Related U.S. Application Data

(60) Provisional application No. 62/480,010, filed on Mar. 31, 2017.

(52) U.S. Cl.
CPC ............... *A61F 2002/30354* (2013.01); *A61F 2002/30403* (2013.01); *A61F 2002/3054* (2013.01); *A61F 2002/30604* (2013.01); *A61F 2002/30617* (2013.01); *A61F 2002/3069* (2013.01); *A61F 2002/3071* (2013.01); *A61F 2/30749* (2013.01); *A61F 2/3859* (2013.01); *A61F 2002/4018* (2013.01); *A61F 2002/4022* (2013.01); *A61F 2002/4029* (2013.01); *A61F 2002/4037* (2013.01); *A61F 2002/4044* (2013.01); *A61F 2002/4051* (2013.01)

(56) References Cited

U.S. PATENT DOCUMENTS

| | | | |
|---|---|---|---|
| 5,358,526 | A | 10/1994 | Tornier |
| 5,480,451 | A | 1/1996 | Grundei et al. |
| 5,910,171 | A | 6/1999 | Kummer et al. |
| 6,187,012 | B1 | 2/2001 | Masini |
| 6,197,062 | B1 | 3/2001 | Fenlin |
| 6,197,063 | B1 | 3/2001 | Dews |
| 6,436,147 | B1 | 8/2002 | Zweymuller |
| 6,530,957 | B1 | 3/2003 | Jack |
| 6,626,946 | B1 | 9/2003 | Walch et al. |
| 6,673,114 | B2 | 1/2004 | Hartdegen et al. |
| 6,676,705 | B1 | 1/2004 | Wolf |
| 6,719,799 | B1 * | 4/2004 | Kropf ............... A61F 2/4014 623/19.12 |
| 6,736,851 | B2 | 5/2004 | Maroney et al. |
| 6,749,637 | B1 | 6/2004 | Bahler |
| 6,899,736 | B1 | 5/2005 | Rauscher et al. |
| 6,942,699 | B2 | 9/2005 | Stone et al. |
| 7,175,663 | B1 | 2/2007 | Stone et al. |
| 7,189,261 | B2 | 3/2007 | Dews et al. |
| 7,431,736 | B2 | 10/2008 | Maroney et al. |
| 7,621,961 | B2 | 11/2009 | Stone et al. |
| 7,758,650 | B2 | 7/2010 | Dews et al. |
| 7,819,923 | B2 | 10/2010 | Stone et al. |
| 8,052,758 | B1 | 11/2011 | Winslow |
| 8,062,376 | B2 | 11/2011 | Shultz et al. |
| 8,070,820 | B2 | 12/2011 | Winslow et al. |
| 8,236,059 | B2 | 8/2012 | Stone et al. |
| 8,246,687 | B2 | 8/2012 | Katrana et al. |
| 8,647,387 | B2 | 2/2014 | Winslow |
| 8,702,804 | B2 | 4/2014 | Smith et al. |
| 8,734,457 | B2 | 5/2014 | Bailey et al. |
| 8,771,362 | B2 | 7/2014 | Isch et al. |
| 8,795,379 | B2 | 8/2014 | Smith et al. |
| 8,876,908 | B2 | 11/2014 | Katrana et al. |
| 8,906,103 | B2 | 12/2014 | Stone et al. |
| 8,968,415 | B2 | 3/2015 | Meridew et al. |
| 9,241,803 | B2 | 1/2016 | Stone et al. |
| 9,283,083 | B2 | 3/2016 | Winslow et al. |
| 9,326,862 | B2 | 5/2016 | Smith et al. |
| 9,408,704 | B2 | 8/2016 | Metzger |
| 9,498,344 | B2 | 11/2016 | Hodorek et al. |
| 9,566,162 | B2 | 2/2017 | Ich |
| 9,693,880 | B2 | 7/2017 | Anthony et al. |
| 10,022,229 | B2 | 7/2018 | Cappelletti |
| 10,070,967 | B2 | 9/2018 | Chavarria et al. |
| 10,226,349 | B2 | 3/2019 | Sperling et al. |
| 10,368,998 | B2 | 8/2019 | Chavarria et al. |
| 10,368,999 | B2 | 8/2019 | Greiwe |
| 10,390,972 | B2 | 8/2019 | Rao |
| 10,433,969 | B2 | 10/2019 | Humphrey |
| 2001/0011193 | A1 | 8/2001 | Nogarin |
| 2002/0156534 | A1 | 10/2002 | Grusin et al. |
| 2003/0028253 | A1 | 2/2003 | Stone et al. |
| 2003/0097183 | A1 | 5/2003 | Rauscher et al. |
| 2004/0064190 | A1 | 4/2004 | Ball et al. |
| 2005/0049713 | A1 | 3/2005 | Garber et al. |
| 2005/0071014 | A1 | 3/2005 | Barnett et al. |
| 2006/0020344 | A1 | 1/2006 | Shultz et al. |
| 2006/0069445 | A1 | 3/2006 | Ondrla et al. |
| 2007/0162140 | A1 | 7/2007 | McDevitt |
| 2007/0173945 | A1 | 7/2007 | Wiley et al. |
| 2007/0179624 | A1 | 8/2007 | Stone et al. |
| 2007/0225821 | A1 | 9/2007 | Reubelt et al. |
| 2008/0228281 | A1 | 9/2008 | Forrer et al. |
| 2009/0281630 | A1 | 11/2009 | Delince et al. |
| 2009/0312838 | A1 | 12/2009 | Klotz |
| 2011/0060417 | A1 | 3/2011 | Simmen et al. |
| 2011/0060418 | A1 | 3/2011 | Bailey et al. |
| 2011/0295376 | A1 | 12/2011 | Winslow |
| 2012/0143204 | A1 | 6/2012 | Blaycock et al. |
| 2012/0232667 | A1 | 9/2012 | Katrana et al. |
| 2013/0090736 | A1 | 4/2013 | Katrana et al. |
| 2013/0150975 | A1 | 6/2013 | Iannotti et al. |
| 2013/0197652 | A1 | 8/2013 | Ekelund et al. |
| 2014/0236304 | A1 | 8/2014 | Hodorek et al. |
| 2015/0265411 | A1 | 9/2015 | Deransart et al. |
| 2016/0213480 | A1 | 7/2016 | Stone et al. |
| 2016/0262902 | A1 | 9/2016 | Winslow et al. |
| 2016/0361173 | A1 | 12/2016 | Reubelt et al. |
| 2017/0049573 | A1 | 2/2017 | Hodorek et al. |
| 2017/0056187 | A1 | 3/2017 | Humphrey et al. |
| 2018/0271667 | A1 | 9/2018 | Kemp et al. |
| 2018/0368982 | A1 | 12/2018 | Ball |
| 2019/0274835 | A1 | 9/2019 | Wiley et al. |

FOREIGN PATENT DOCUMENTS

| | | |
|---|---|---|
| EP | 1415621 | 5/2004 |
| EP | 1782765 | 5/2007 |
| EP | 2604225 | 6/2013 |
| FR | 2652498 | 4/1991 |
| FR | 2773469 | 7/1999 |
| JP | 2003517337 A | 5/2003 |
| JP | 2009523578 A | 6/2009 |
| JP | 2009297515 A | 12/2009 |
| JP | 2011512926 A | 4/2011 |
| WO | WO 93/09733 | 5/1993 |
| WO | WO 96/17553 | 6/1996 |
| WO | WO 2003/005933 | 1/2003 |
| WO | 2007084939 A2 | 7/2007 |
| WO | WO 2008/000928 | 1/2008 |
| WO | WO 2013/064569 | 5/2013 |
| WO | WO 2014/067961 | 5/2014 |
| WO | 2016094739 A1 | 6/2016 |
| WO | WO 2018/183484 | 10/2018 |
| WO | WO 2019/079104 | 4/2019 |

OTHER PUBLICATIONS

First Office Action issued in connection in Japanese Patent Application No. 2021-518133, dated May 31, 2022, 6 pages.
First Examination Report issued in connection with Australian Patent Application No. 2022202353, dated Jun. 13, 2023, 5 pages.
Non-Final Office Action issued in connection with U.S. Appl. No. 17/278,495, filed Nov. 3, 2023, 17 pages.

* cited by examiner

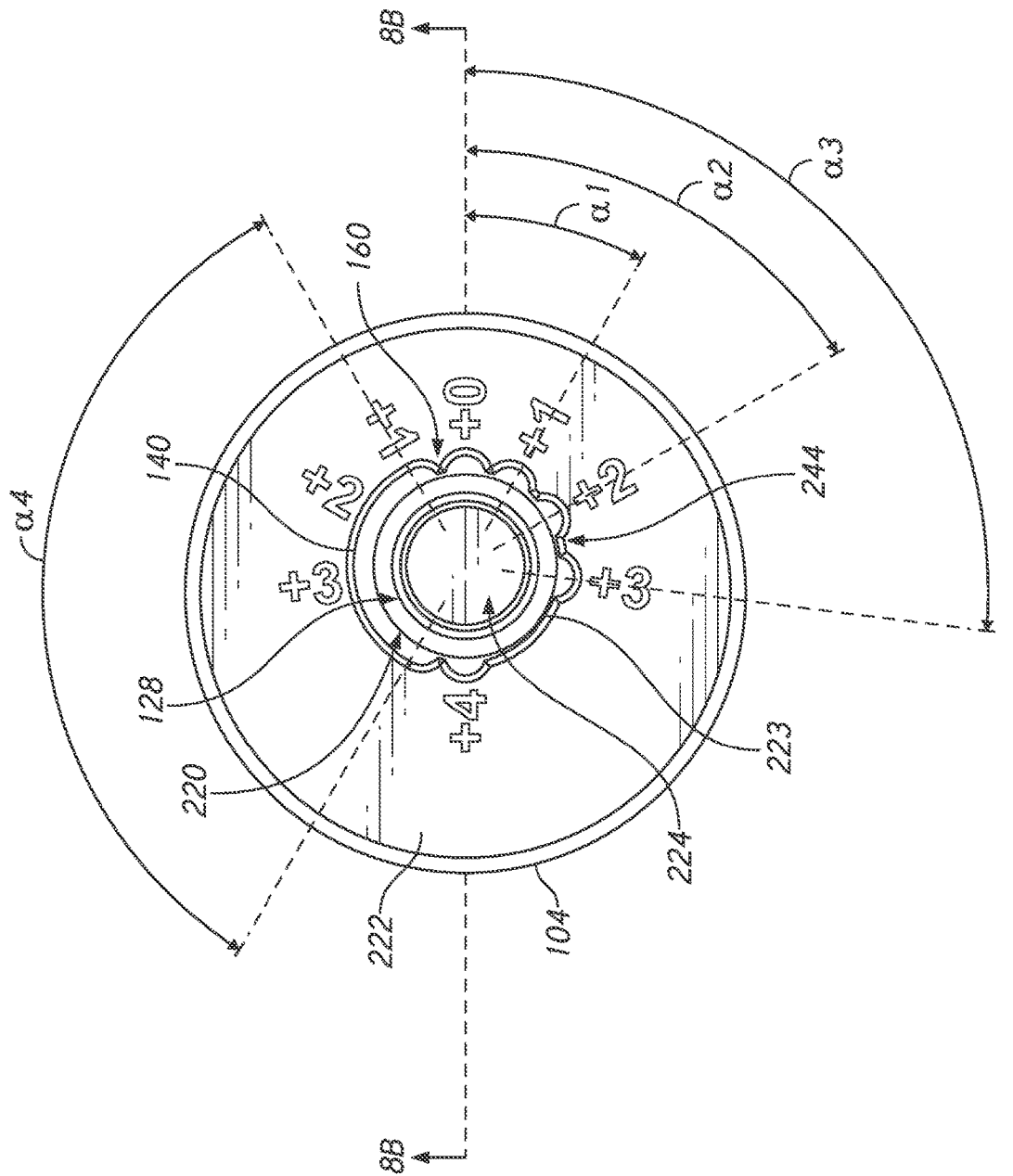

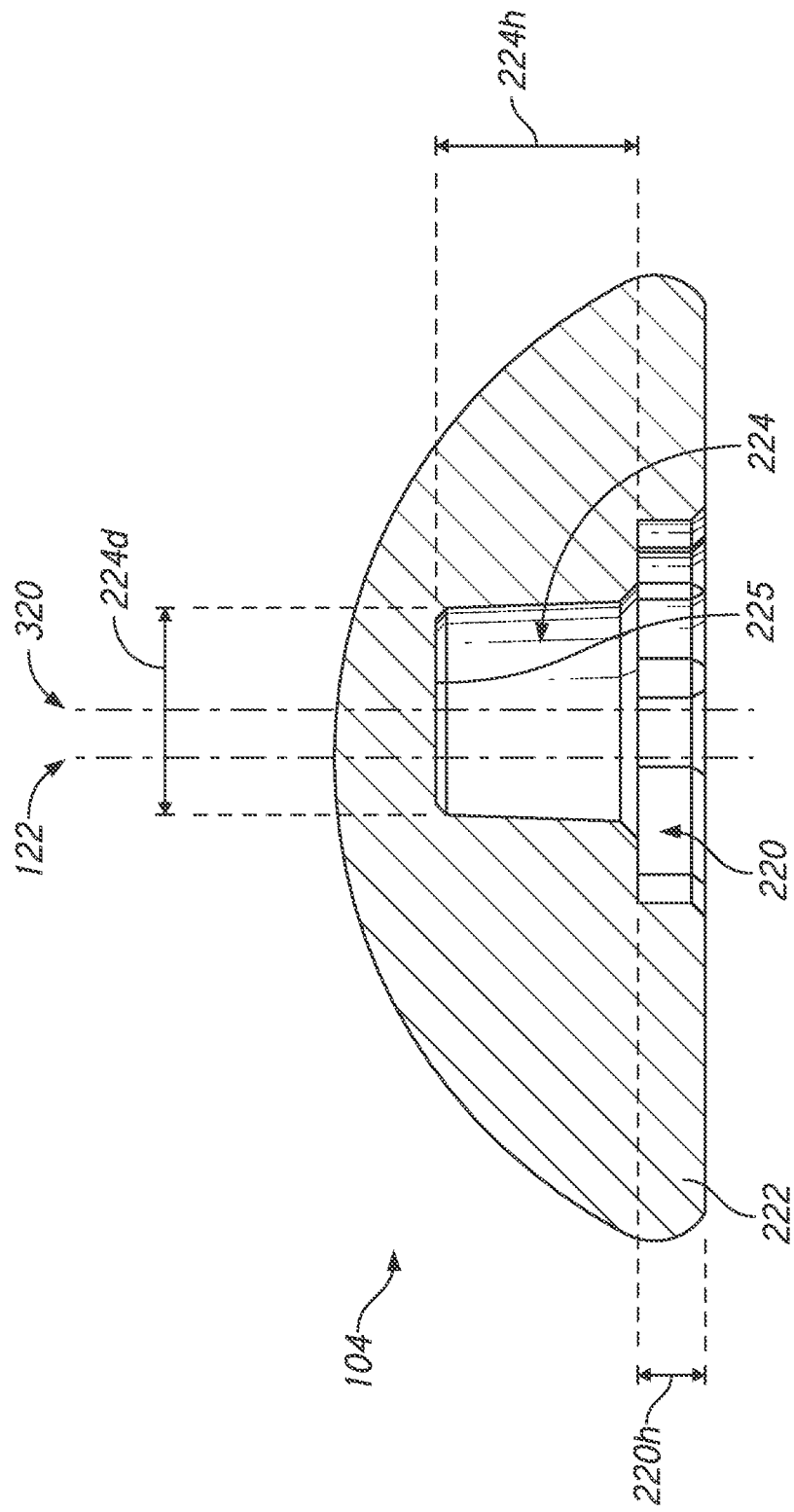

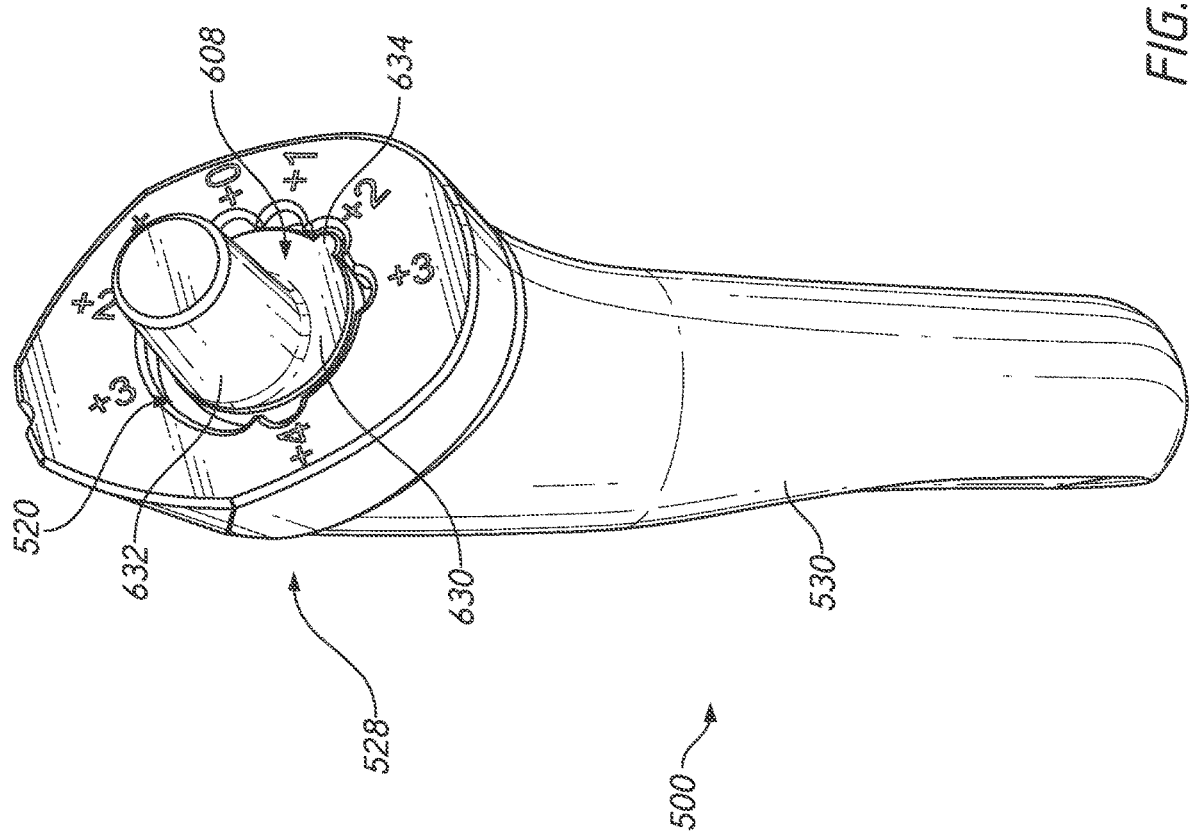

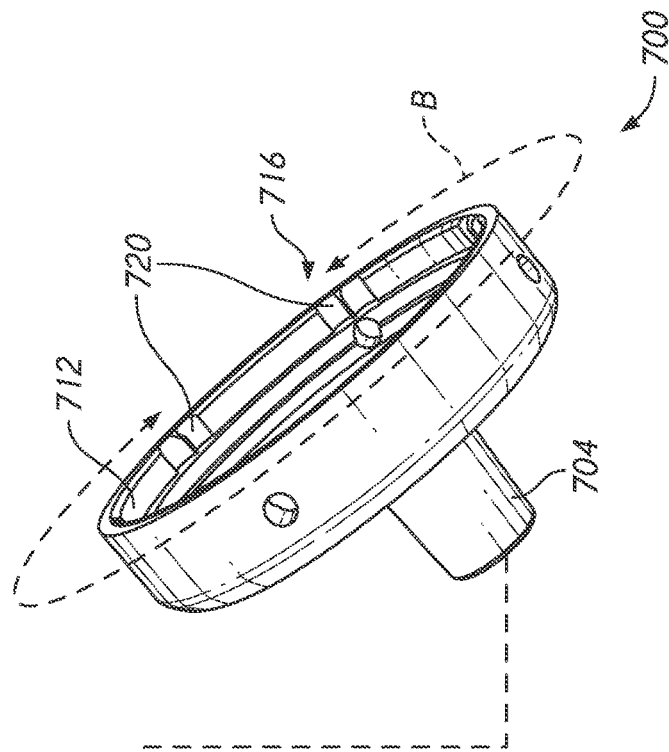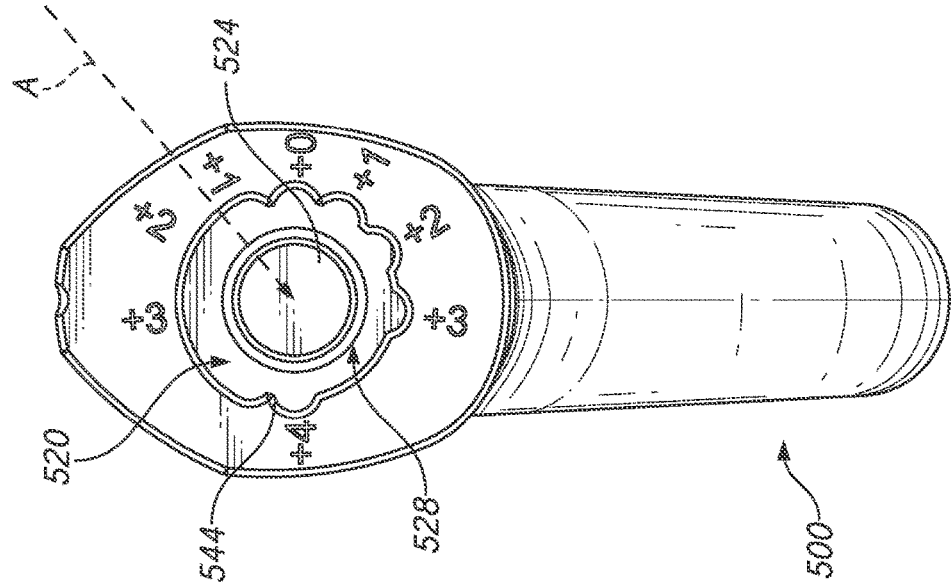
FIG. 14A

MODULAR HUMERAL HEAD AND RELATED METHODS

CROSS-REFERENCE TO RELATED APPLICATIONS

This application is a divisional of co-pending U.S. patent application Ser. No. 15/938,214, filed on Mar. 28, 2018, the entire contents of which are incorporated herein by reference.

BACKGROUND

Field

The present disclosure relates to humeral head assemblies and components thereof as well as methods for assembling and implanting them.

Description of the Related Art

Skeletal joints have a variety of configurations providing for a wide range of smooth movement of two or more bones relative to each other. For example, in a shoulder joint, an articulating surface at one end of the humerus interacts with an articulating surface at the glenoid cavity of the scapula in a manner similar to a "ball and socket" joint. Joint conditions can develop that cause pain and restrict motion of the shoulder joint. Implanting prosthetic components at one or both articulating surface of the joint can improve such conditions.

A typical anatomical shoulder joint replacement attempts to mimic the natural joint anatomy. For example, a humeral anchor (e.g., a stem or stemless anchor) can be attached to the humerus and a convex humeral head and assembled to the anchor. Together these structures can replace the humeral articulating surface of the shoulder joint. The humeral head can articulate with the native glenoid socket or with a glenoid resurfacing device that replaces the articulating surface of the glenoid.

The position of the humeral head relative to humerus is important to the security of the humeral head assembly and to the motion of the joint post operatively.

SUMMARY

There is a need for greater flexibility in placement of a humeral head relative to a humeral anchor for a shoulder joint. There is a need for humeral head assemblies that allow for an articular surface of the head to be either centered on or eccentric from an axis along which the humeral head is coupled with a humeral anchor. There is a need for humeral head assemblies that provide for a range of eccentricity to an assembly axis so that a wide range of patient needs can be met by the assembly.

In some embodiments, a humeral head assembly is provided that can include an articular body and a coupler. The articular body can include a convex articular surface and a coupling portion. The coupling portion can be disposed on a side of the articular body opposite the convex articular surface. In some examples, the coupling portion can include a continuous zone of eccentricity adjustment. In some embodiments, the continuous zone of eccentricity adjustment includes at least one discrete position site. The coupler can include a first portion and a second portion. The first portion can be configured to mate with the coupling portion. The second portion can be located opposite the first portion and can be configured to mate with another member of a joint prosthesis.

In some embodiments, the first portion of the coupler includes a tapered protrusion that couples with the articular body by an interference fit. The second portion of the coupler can be tapered. In some examples, the first portion of the coupler is placed in a first configuration against the coupling portion and the rotational position of the coupler to the articular body is adjusted along the continuous zone to allow for selection of different amounts of eccentricity along the continuous zone and the coupler can be secured to the articular body at the coupling portion in a second configuration. In other embodiments, the coupling portion includes a plurality of continuous zones of eccentricity adjustment.

The coupler can also include a collar disposed between the first portion and the second portion thereof, the collar including a protrusion configured to be positionable at least along the continuous zone of eccentricity adjustment. In some examples, the coupling portion includes a radial notch configured to receive the protrusion. Relative rotation of the coupler to the articular body is prevented when the protrusion is received in the notch. The position of the protrusion and the notch can be reversed, such that the coupling portion includes one or a plurality of protrusions at the discrete position site(s) and the collar includes a notch configured to receive a protrusion. In some embodiments, the radial notch is disposed circumferentially adjacent to the continuous zone of eccentricity adjustment. In other embodiments, the radial notch is disposed at a position where no eccentricity is provided between the coupler and the articular body when the protrusion is disposed in the notch.

In some examples, the continuous zone of eccentricity adjustment and the at least one discrete position site are disposed in a same plane. In some embodiments, the plurality of discrete eccentricity positions is disposed on the side of the articular body opposite the convex articular surface and the plurality extends along an angular range opposite the continuous zone of eccentricity adjustment. The continuous range can provide at least 90 degrees of eccentricity. In other embodiments, the continuous range provides from about 90 to about 180 degrees of eccentricity. In some embodiments, the plurality of discrete eccentricity positions includes at least three discrete sites corresponding to positions of eccentricity in a first direction. In some examples, the at least three discrete sites corresponding to positions of eccentricity are disposed between a site corresponding to a position of no eccentricity and a site corresponding to a position of maximum eccentricity. In some embodiments, the position of no eccentricity is 180 degrees rotationally offset from the position of maximum eccentricity.

In some embodiments, the coupling portion includes a discrete eccentricity position in which the first portion of the coupler can be placed in the first configuration against the coupling portion and the rotational position of the coupler to the articular body is fixed. In some examples, the coupling portion includes a plurality of continuous zones of eccentricity adjustment, one of the zones of the plurality being disposed on each side of the discrete eccentricity position. In some embodiments, the coupling portion includes a plurality of discrete eccentricity positions, the continuous zone of eccentricity adjustment being between the discrete eccentricity positions. In some embodiments, the coupling portion includes a plurality of discrete eccentricity positions and a plurality of continuous zones of eccentricity adjustment, the discrete eccentricity positions alternating with the continuous zones of eccentricity adjustment.

The humeral head assemblies described herein can include indicia indicating an amount of eccentricity. The amount of eccentricity can be indicated at predetermined spaced apart locations of the continuous zone. The indicia can be disposed on a side of the articular body opposite the convex articular surface. In some embodiments, the indicia comprise a plurality of markings on the side of the articular body opposite the convex articular surface. The amount of eccentricity provided by a specific rotational position of the coupler relative to the articular body can be provided when the protrusion is aligned with one of the plurality of indicia.

In another embodiment, a humeral head assembly is provided that can include an articular body and a coupler. The articular body can include a convex articular surface and a coupling portion. The coupling portion can be disposed on a side of the articular body opposite the convex articular surface. The coupling portion can include a recess extending from the side opposite the convex articular surface toward the convex articular surface. The recess can have an outer periphery having at least one radial notch disposed therealong. The coupler can include a first portion configured to mate with the coupling portion. The coupler can include a radial protrusion disposed thereon. The second portion can be located opposite the first portion and can be configured to mate with another member of a joint prosthesis. The first portion of the coupler can be placed against the coupling portion such that the radial protrusion can be received in the radial notch.

In another embodiment, a humeral head assembly is provided that can include an articular body, a bone anchor, a coupling portion, and a coupler. The articular body can include an articular surface and a coupling portion. The coupling portion disposed on a side of the articular body opposite the articular surface. The bone anchor includes a distal end configured to be lodged in a bone and a proximal face. The coupling portion includes a continuous zone of eccentricity adjustment and at least one discrete position site disposed between the convex articular surface and the distal end of the bone anchor. The coupler includes a first portion configured to mate with the coupling portion and a second portion opposite the first portion. The second portion is configured to couple the articular body with the bone anchor.

In other embodiments, the bone anchor includes a stem portion configured to be disposed in an intramedullary canal. In other embodiments, the bone anchor includes a stemless anchor configured such that a distal portion resides in the metaphyseal portion or medial of the metaphyseal portion. The coupling portion of the bone anchor can be disposed on a medial surface of the bone anchor. In other embodiments, the bone anchor includes a continuous zone of eccentricity adjustment including an arcuate segment of a circular recess providing for rotation of a radial protrusion of the coupler therein. The bone anchor can include at least one discrete position site that includes a radial notch aligned with the continuous zone of eccentricity adjustment.

In some embodiments, an articular component of a prosthetic shoulder joint can be assembled by engaging a first end of a coupler with a coupling portion of an articular body. The assembly of the prosthetic shoulder joint can include providing relative rotation between the articular body about the first end of the coupler along a continuous range of rotational positions while the first end is engaged with the coupling portion or providing relative rotation to align the coupler with a discrete position feature. Assembling the articular component can include selecting an amount of eccentricity corresponding to a position within the continuous range of rotational position. Assembling the articular component can include selecting an amount of eccentricity corresponding to the discrete position feature. Assembling the articular component can include securing the articular body about the first end of the coupler at the selected amount of eccentricity or discrete position feature.

Assembling the articular component can also include positioning a protrusion of the coupler along the continuous zone, wherein the protrusion is disposed between the first end and a second end of the coupler. In some embodiments, assembling the articular component includes engaging the protrusion in a radial notch of the coupling portion thereby preventing relative rotation of the coupler to the articular body. In some examples, assembling the articular component includes aligning an alignment feature of the coupler with an eccentricity amount indicator disposed on or adjacent to the coupling portion of the articular body. Assembling the articular component can also include aligning a radial protrusion of the coupler with one of a plurality of indicia of eccentricity disposed on the articular body.

The prosthetic shoulder joint can include a number of additional features. In some examples, the continuous range provides at least 90 degrees of relative rotation. In some embodiments, a discrete position feature is disposed at a position where no eccentricity is provided between the coupler and the articular body. In some embodiments, a radial notch can be disposed circumferentially adjacent to the continuous zone of eccentricity adjustment.

In some embodiments, the coupling portion includes a plurality of discrete position features, and where providing relative rotation to align the coupler with a discrete position feature comprises selecting between a discrete position of no eccentricity and a discrete position of eccentricity. In other embodiments, the coupling portion includes a plurality of discrete position features, each of the discrete position features providing a different amount of eccentricity, and where providing relative rotation to align the coupler with a discrete position feature comprises selecting between a discrete position feature corresponding to lesser eccentricity and a discrete position feature corresponding to greater eccentricity.

In another embodiment, an articular component is provided that includes an articular body, a bone anchor, and a coupling portion. The articular body includes an articular surface, e.g., a convex or a concave articular surface. The bone anchor has a distal end configured to be lodged in a bone and a proximal face. The coupling portion has a continuous zone of eccentricity adjustment and at least one additional position site disposed between the articular surface and the distal end of the bone anchor. The coupler has a first portion configured to mate with the coupling portion and a second portion opposite the first portion. The second portion configured to couple, directly or indirectly, the articular body with the bone anchor.

In articular components, the coupling portion can be disposed on the articular body on a side of the articular body opposite a convex articular surface.

In one variation, a method of assembling an articular component of a prosthetic shoulder joint is provided. A first end of a coupler is engaged with a coupling portion. The coupling portion can be on the articular body or on an intermediate coupler to which the articular body is connected. Relative rotation can be provided between the articular body and the coupler about the first end of the coupler. The rotation can be along a continuous range of rotational positions while the first end is engaged with the coupling portion. The relative rotation can be to align the coupler with a discrete position feature. An amount of eccentricity corresponding to a position within the continuous range of rotational position or to the discrete position feature is selected. The articular body is secured about the first end of the coupler at the selected amount of eccentricity or discrete position feature.

In another embodiment a method of assembling an articular component of a prosthetic shoulder joint is provided. In the method, an end of a coupler of a joint implant is engaged with a coupling portion of another component of the joint implant. Relative rotation is provided between the end of the coupler and the coupling portion of the other component of the joint implant along a continuous range of rotational positions while the end is engaged with the coupling portion of the other component of the joint implant. An amount of eccentricity corresponding to a position within the continuous range of rotational position is selected. The other component of the joint implant is secured to the end of the coupler at the selected amount of eccentricity.

Any feature, structure, or step disclosed herein can be replaced with or combined with any other feature, structure, or step disclosed herein, or omitted. Further, for purposes of summarizing the disclosure, certain aspects, advantages, and features of the inventions have been described herein. It is to be understood that not necessarily any or all such advantages are achieved in accordance with any particular embodiment of the inventions disclosed herein. No aspects of this disclosure are essential or indispensable.

BRIEF DESCRIPTION OF THE DRAWINGS

These and other features, aspects and advantages are described below with reference to the drawings, which are intended for illustrative purposes and should in no way be interpreted as limiting the scope of the embodiments. Furthermore, various features of different disclosed embodiments can be combined to form additional embodiments, which are part of this disclosure. In the drawings, like reference characters denote corresponding features consistently throughout similar embodiments. The following is a brief description of each of the drawings.

FIG. 8A is a bottom view of an articular body of the humeral head assembly of FIG. 2;

FIG. 8B is a cross-sectional view of an articular body of the humeral head assembly of FIG. 2 through plane 8B-8B shown in FIG. 8A;

FIGS. 13A-13C illustrate an embodiment of the coupling portion on a surface of a stem; and FIGS. 14A-14C show humeral implant assemblies and components thereof suitable for adjusting offset of a reverse articular body humeral assembly.

DETAILED DESCRIPTION OF THE PREFERRED EMBODIMENT

This application is directed to orthopedic assemblies that enable a first portion thereof to be selectively coupled with a second portion to selectively position the first portion aligned with or eccentric to the second portion. The first portion can be co-linear with the second portion. In applications discussed in detail below, the first portion can include an articular body and the second portion can include a bone anchor portion to be coupled to a bone. For example in the context of the shoulder, a humeral head assembly can be provided that enables an articular surface or other aspect of an articular body to be coupled with a humeral anchor in a centered position or in an eccentric position. In some variations, a glenoid anchor could be provided and a shoulder assembly could enable an articular body such as a glenosphere of a reverse shoulder implant to be disposed in a centered or eccentric position relative to the anchor. In further variations, an assembly can be adapted for positioning an articular body of a femoral assembly relative to a femur anchor to provide for centered or eccentric positioning thereof for a hip or a knee assembly. In further variations, an assembly can be adapted for positioning an articular body of a tibial assembly relative to a tibial anchor to provide for centered or eccentric positioning thereof for a knee assembly. The ability to couple the articular surface in a centered or at one or more eccentric positions, or over a range of eccentric positions, allows a surgeon to treat a wider variety of patient anatomy with a kit that has fewer components than was possible in the past.

I. Centered Versus Eccentric Humeral Assemblies

Figure 1:
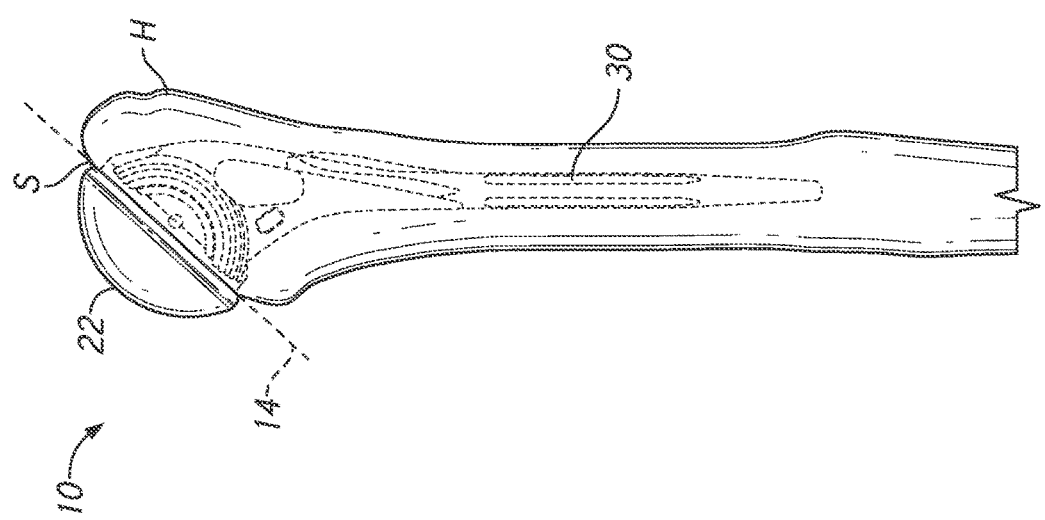
FIG. 1 is a side view of a humerus with a humeral head assembly implanted therein.

FIG. 1 shows an example of a humeral head assembly 10 coupled with a humerus H. In a process of implanting the head assembly 10 in the humerus H, the shoulder joint space is surgically accessed and the humerus is separated from the glenoid cavity of the scapula. The head of the humerus H is separated from the rest of the humerus by cutting, or resecting, along a plane 14. This resection creates an exposed surface S of the proximal humerus H. Thereafter, the intramedullary canal of the humerus (an elongated hollow space in the humerus) is accessed and may be enlarged or otherwise prepared. Thereafter, a stem 30 can be inserted into the canal leaving a coupling face 40 (See FIGS. 1A and 1B) of the stem 30 exposed at or accessible from the surface S. In alternative techniques, a stemless anchor is provided that does not require access to or preparation of the intramedullary canal. An articular body 22 can then be coupled with the stem 30 to form a humeral head assembly coupled with the humerus H, as shown in FIG. 1.

Figure 1B:
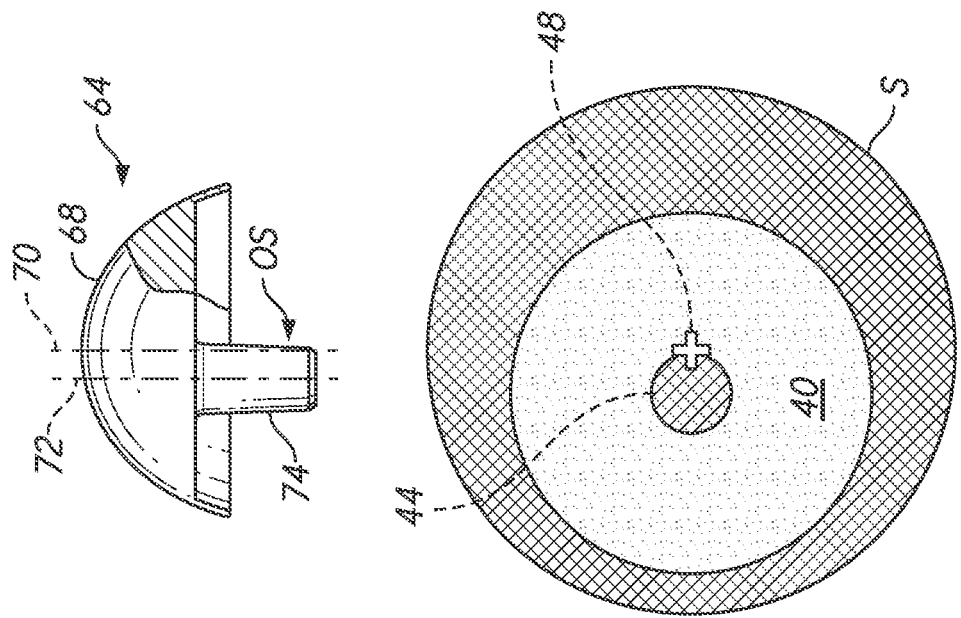
FIG. 1B shows a humeral head having an eccentric coupler and an implantation site that would benefit from coupling with an eccentric coupler humeral head.
Figure 1A:
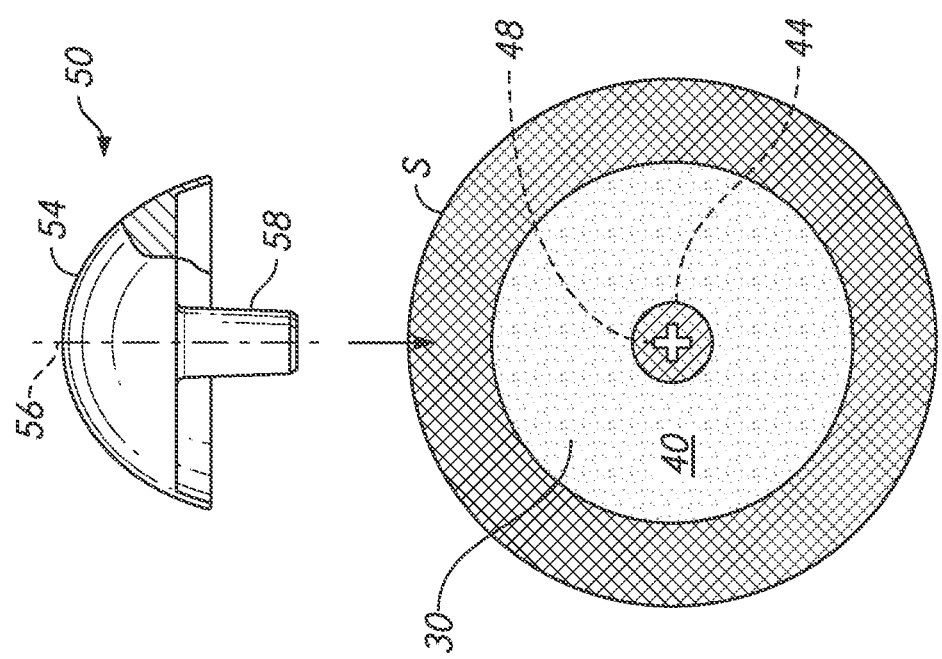
FIG. 1A shows a humeral head having a centered coupler and an implantation site suitable for a centered coupler.

Whether a stemless or a stemmed humeral anchor is used, the coupling face of that anchor, which is disposed at the surface S, may not necessarily be in the center of the surface S. This variable can be addressed by providing a kit having some humeral heads that are centered and some that are eccentric. FIG. 1A shows the stem 30 placed in the humerus H in a centered position. A coupling feature 44 at a center of the coupling face 40 of the stem 30 is aligned with a center 48 of the exposed surface S of the humerus H. In this configuration a humeral head 50 with a centered articular surface 54 can be used, e.g., is selected from the kit. A center of the articular surface 54 is intersected by, e.g., is co-linear with, a longitudinal axis 56 of a stem 58 of the humeral head 50. FIG. 1B shows that in some cases, the process of resecting the humerus H and placing the stem 30 results in the coupling feature 44 being off-set from the center 48 of the exposed surface S of the humerus H. In this configuration a humeral head 64 with an eccentric articular surface 68 can be used, e.g., is selected from the kit. A center 70 of the articular surface 68 is not intersected by, e.g., is not co-linear with, a longitudinal axis 72 of a stem 74 of the humeral head 64. Rather, there is a offset OS between the center 70 and the longitudinal axis 72. The offset OS shifts the articular surface 68 toward the center 48 of the surface S of the humerus H, which is a preferred placement in many situations.

A kit with a plurality of humeral heads 50, 64 can be provided. But, such a kit will contain at least one extra humeral head which is an inefficient approach.

II. Humeral Head Assemblies with Adjustable Eccentricity

The following embodiments facilitate providing a centered or a range of eccentric positions of a humeral head relative to a resected humeral surface that is more effective than past practice. The embodiment discussed below could be used in other orthopedic applications, including for providing centered or eccentric positioning of a glenosphere on a glenoid or scapular anchor, for providing centered or eccentric positioning of a femoral articular body on a femur anchor, for providing centered or eccentric positioning of tibial articular body on a tibial anchor, or for other orthopedic applications.

A. Continuous Adjustment and Discrete Adjustment of a Humeral Head

Figure 2:
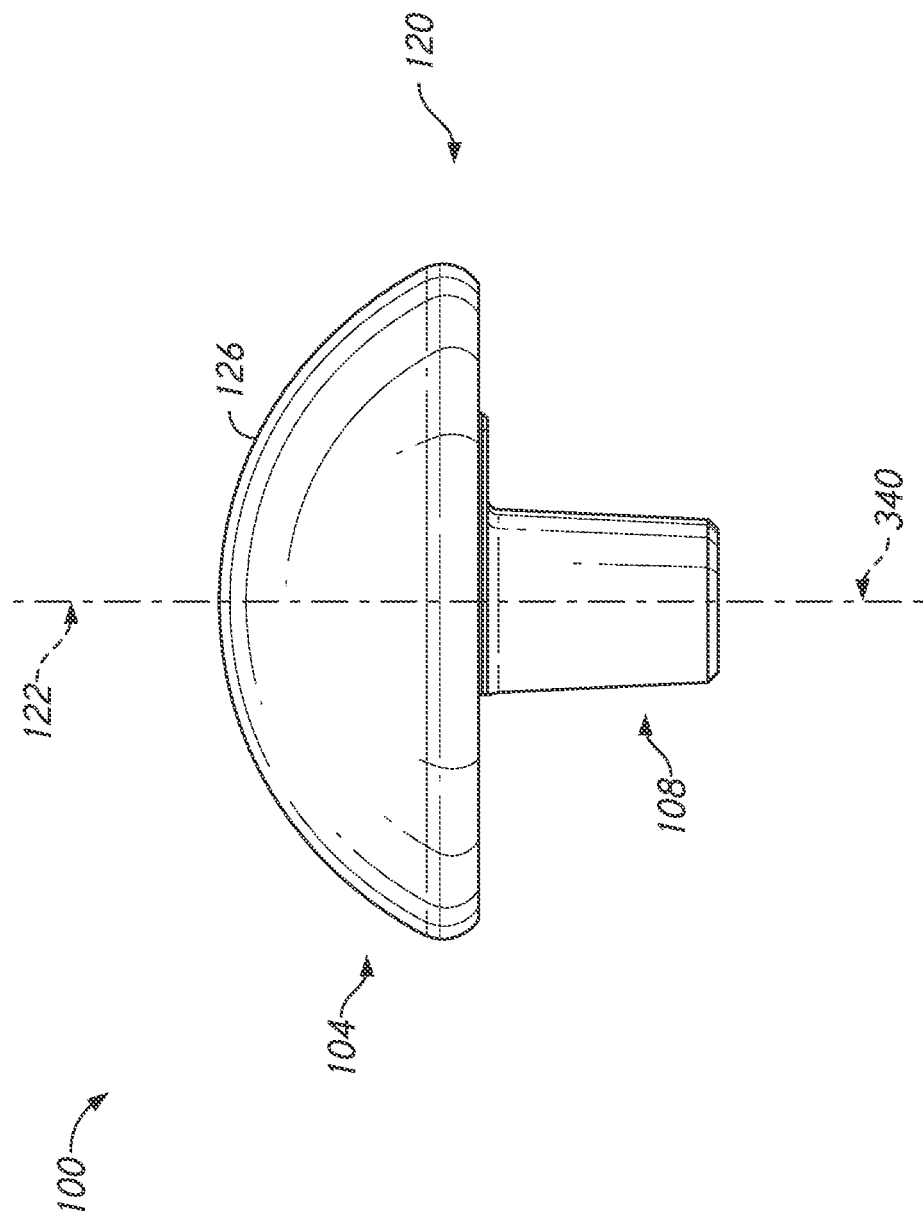
FIG. 2 shows one embodiment of a humeral head assembly, showing a first configuration in which an eccentricity of a portion of a coupler adapted to mate with a humeral anchor to the articular surface of an articular body is zero.
Figure 3:
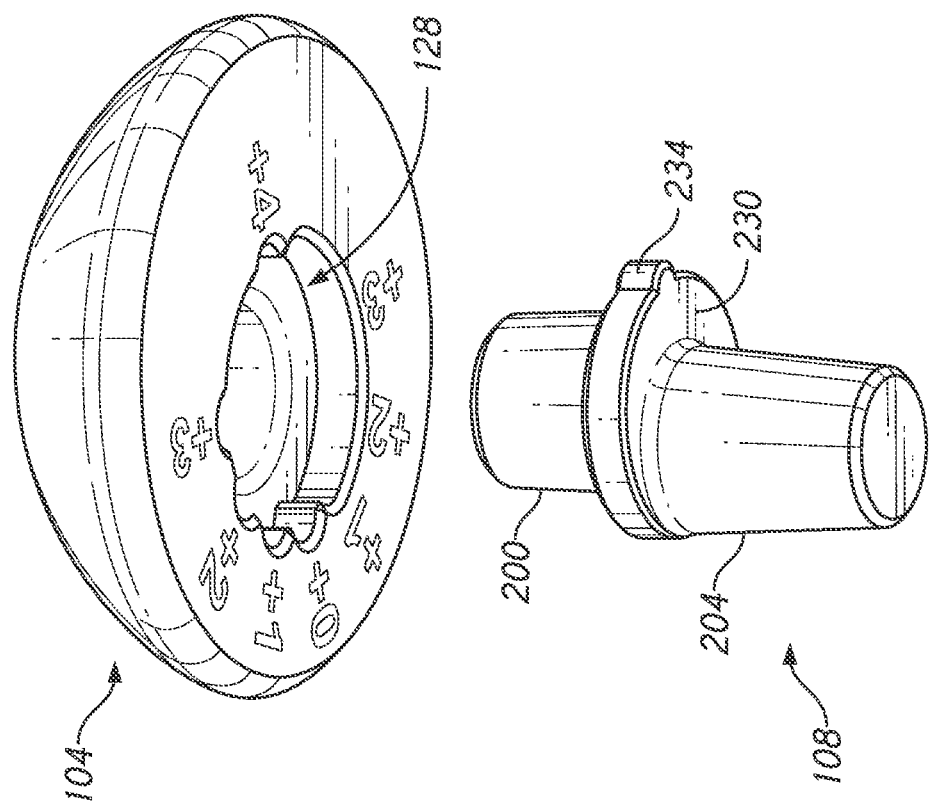
FIG. 3 is an exploded bottom view of the humeral head assembly of FIG. 2
Figure 4A:
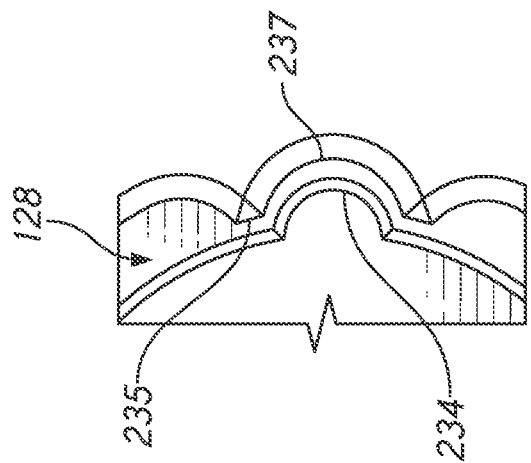
FIG. 4A shows detail 4A of FIG. 4 illustrating radial overlap between a protrusion of a coupler and a circumferential edge of an articular body.
Figure 4:
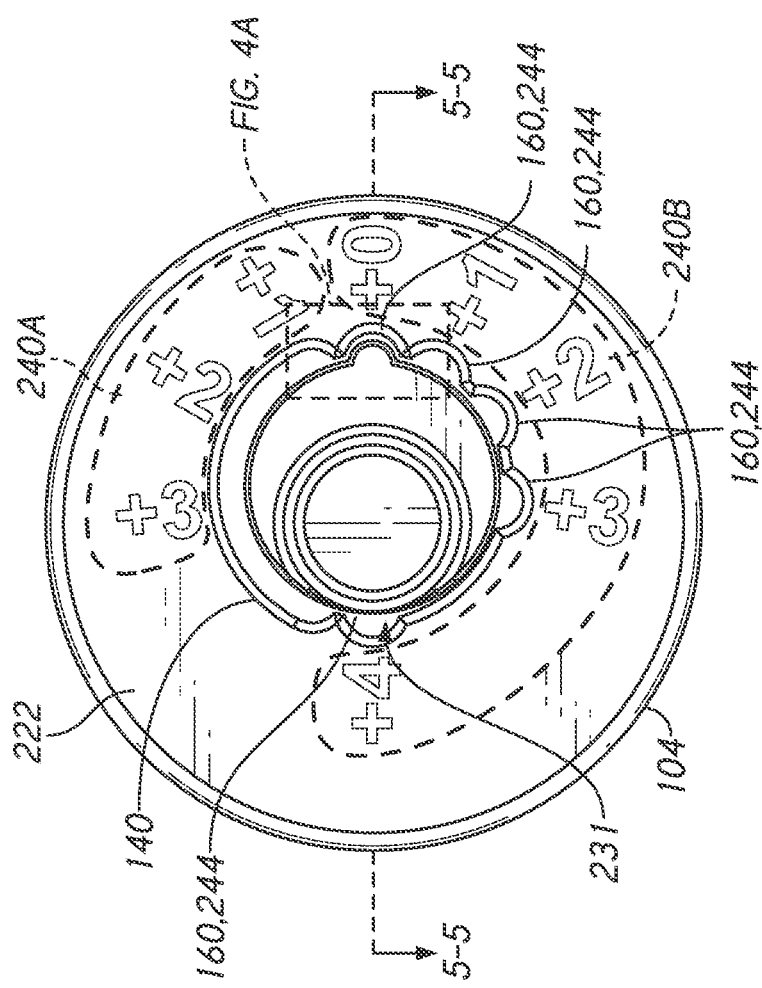
FIG. 4 is a lateral side view of the humeral head assembly of FIG. 2.
Figure 5A:
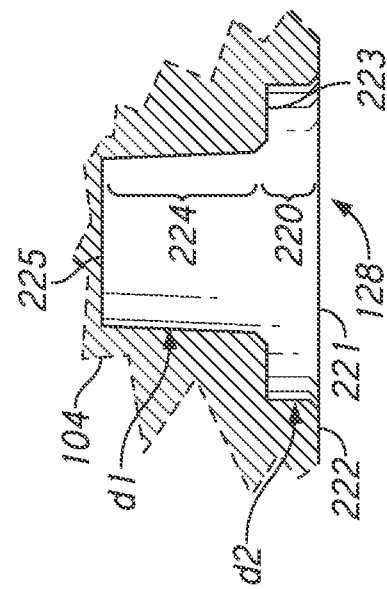
FIG. 5A is a detail view of recesses of a coupling portion of an articular body.
Figure 5:
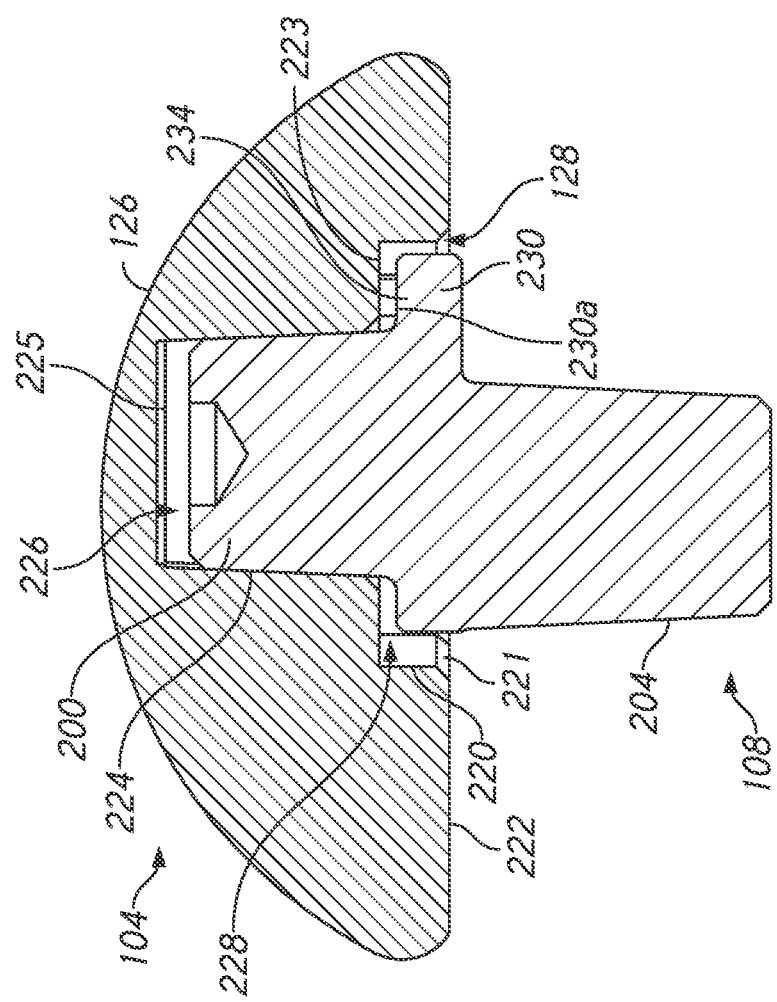
FIG. 5 is a cross-section taken through plane 5-5 shown in FIG. 4.
Figure 6:
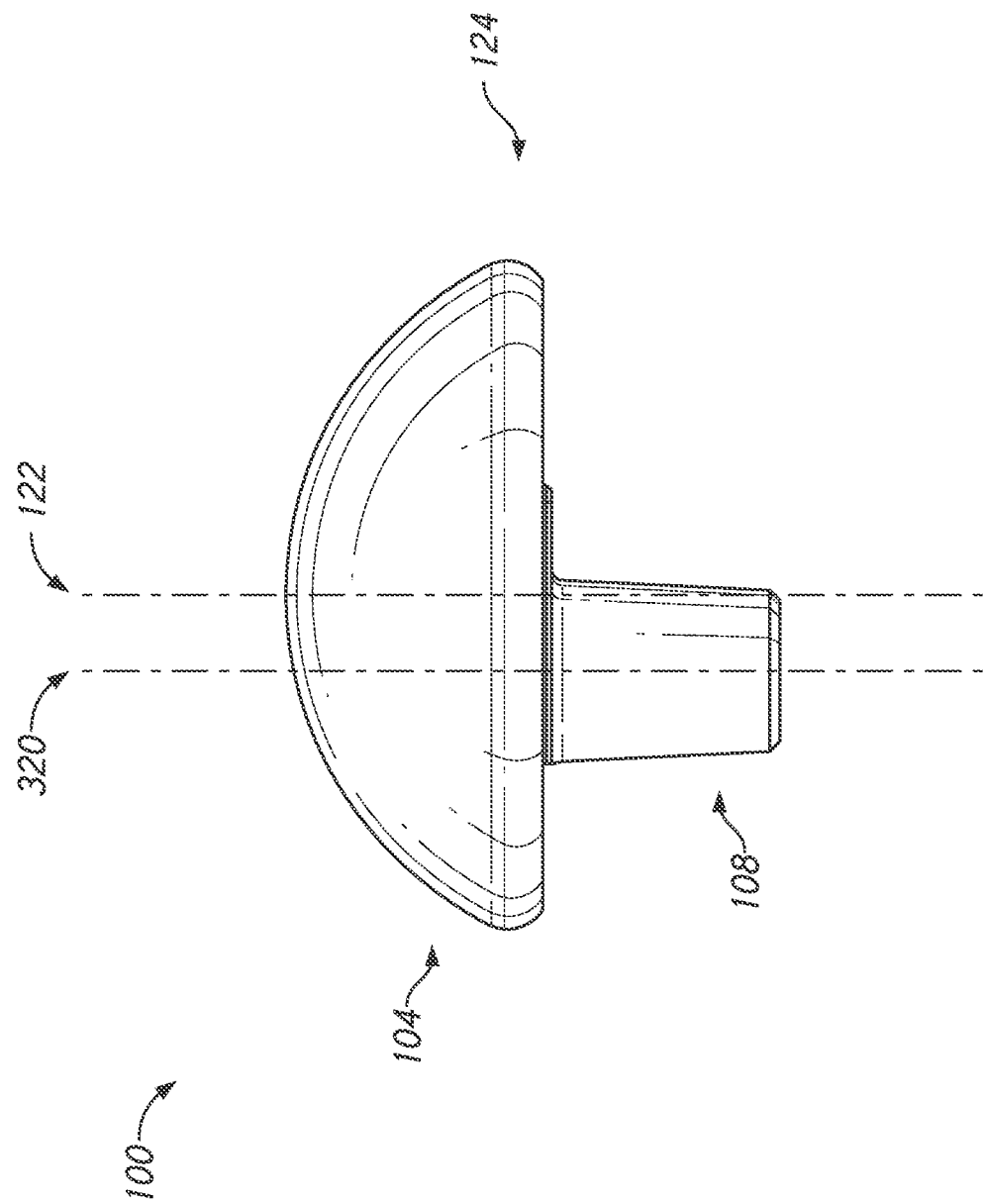
FIG. 6 shows one embodiment of the humeral head assembly of FIG. 2, showing a second configuration in which an eccentricity of the portion of the coupler adapted to mate with a humeral anchor to the articular surface of the articular body is non-zero.

FIGS. 2-11 show embodiments of a humeral head assembly 100 in which eccentricity of the assembly can be adjusted as needed during implantation. FIG. 3 shows that an articular body 104 and a coupler 108 are separable components of the assembly 100. The articular body 104 and the coupler 108 can be coupled in a number of different positions to facilitate the adjustment of or elimination of eccentricity. As discussed further below, the different positions can be arrived at along a continuous range of adjustment, by selecting a discrete position of one or more discrete positions, or by selecting among these modes of adjustment. FIGS. 2, 4 and 5 illustrate a first configuration 120 of the humeral head assembly 100. The first configuration 120 corresponds to a centered (or not eccentric) position. FIG. 6 illustrates a second configuration 124 an embodiment of the humeral head assembly 100. The second configuration 124 corresponds to an eccentric position.

FIG. 2 shows that the articular body 104 can have an articular surface 126. The articular surface 126 can be a convex surface. The articular surface 126 can be configured to engage with a concave surface of or at a glenoid of a patient. FIG. 3 shows that the articular body 104 also has a coupling portion 128. The coupling portion 128 is disposed on a side of the articular body 104 opposite the convex articular surface 126. The coupling portion 128 has a continuous zone 140 of eccentricity adjustment, shown in FIG. 4. For example, shading in FIG. 4 indicates the zone 140 which is an area over which the articular body 104 can be positioned relative to the coupler 108. The humeral head assembly 100 also has at least one site 160 for discrete positioning of the articular body 104 on the coupler 108. There can be one, two, three, four, five, or more than five sites 160. The discrete position site 160 allows for connecting the coupler 108 to the articular body 104 at one or more pre-defined positions and prevents relative rotation when so engaged. In some embodiments, the continuous zone 140 of eccentricity adjustment and the at least one discrete position site 160 are disposed in a same plane, e.g., in a plane transverse a normal to the center of the articular surface 126. An amount of eccentricity can be selected in the continuous zone 140 or in the discrete position site(s) 160 at the same relative axial position of the coupler 108 and the articular body 104. In some examples, the continuous zone 140 of eccentricity adjustment is located between discrete position sites 160. FIG. 4 shows the coupler 108 engaged with the articular body 104 at one of five discrete position sites 160.

FIGS. 3 and 5 shows that the coupler 108 can have a first portion 200 configured to mate with the articular body 104 and a second portion 204 opposite the first portion 200. The first portion 200 can mate with the coupling portion 128 in one embodiment. The second portion 204 can mate with another member of a joint prosthesis (e.g. with the coupling feature 44 of the humeral stem 30 disposed at a surface S of the humerus H or with a stemless humeral anchor). In other applications, the second portion 204 can mate with another anchor member, such as at a glenoid or scapula, at an end of a femur or at an end of a tibia. In some embodiments, the coupler 108 is asymmetrical such that the second portion 204 has a longitudinal axis that is offset from a longitudinal axis of the first portion 200. As will be discussed in more detail below, this offset can form a lateral offset between the center of the articular body 104 and the longitudinal axis of the second portion 204 when the humeral head assembly 100 is in an eccentric configuration, e.g., the second configuration 124.

The articular body 104 can be configured to engage with and/or be retained by the coupler 108. In some embodiments, the coupler 108 can engage with the coupling portion 128 of the articular body 104 to arrange or maintain the humeral head assembly 100 in the first centered (or non-eccentric) configuration 120 or in the second eccentric configuration 124.

FIGS. 5 and 5A illustrate that the coupling portion 128 can include a first recess 220 disposed within the articular body 104. The first recess 220 can have an open end 221 on a lateral side 222 of the articular body 104. The lateral side 222 is a side of the articular body 104 opposite the articular surface 126. The lateral side 222 faces away from the glenoid when the humeral head assembly 100 is implanted. The first recess 220 can extend to a recessed surface 223. A second recess 224 can extend from the recessed surface 223 into the articular body 104. The second recess 224 can have a closed end 225 and a diameter d1 that is less than a diameter d2 of the first recess 220. In some embodiments, the second recess 224 can be tapered such that the diameter decreases over the length of the second recess 224 to a lesser diameter adjacent to the closed end. The second recess 224 can have a greater diameter toward the recessed surface 223 or toward the first recess 220.

In some examples, the first portion 200 of the coupler 108 can be secured within the second recess 224 of the articular body 104. In some embodiments, the coupler 108 can include a collar 230 that can be configured to be disposed in the first recess 220. The collar 230 can be located between the first portion 200 and the second portion 204 of the coupler 108, e.g., at a proximal end of the first portion 200 or at a distal end of the second portion 204. The collar 230 can be used to position of the articular body 104 on or over the coupler 108. In some embodiments, the collar 230 can include a protrusion 234 configured to secure the articular body 104 at any of the discrete position site(s) 160 of the articular body 104. The protrusion 234 extends in a radial direction. The protrusion 234 extends in a plane perpendicular to a longitudinal axis of the coupler 108. The protrusion 234 can fix a rotational position relative to the articular body 104 by circumferentially overlapping with a radial edge (e.g., a portion of a concavity, such as a notch, cavity, or recess) of the coupling portion 128. FIG. 4A shows that the protrusion 234 can be configured to extend radially outward of a radially inward portion 235 of a circumferential edge 237 (e.g., a portion of a concavity, such as a notch, cavity, or recess disposed in the circumferential edge 237) of the coupling portion 128.

In some embodiments, when the first portion 200 of the coupler 108 is engaged with the second recess 224 of the articular body 104, there is a clearance distance 226 between the closed end 225 of the second recess 224 and the top of the first portion 200 such that the top of the first portion 200 does not engage the closed end 225 f the second recess 224. Similarly, in some embodiments, when the collar 230 of the coupler 108 is engaged with the first recess 220 of the articular body 104, there is a clearance distance 228 between the recessed surface 223 and a top (or medial) side 230a of the collar 230 such that the top (or medial side) of the collar 230 does not engage with the recessed surface 223. Further, the coupler 108 can be engaged with the articular body 104 in a first engaged configuration that permits relative rotation, e.g., along the zone 140. In the first engaged configuration the articular body 104 can be merely place or rested on the first portion 200 of the coupler 108. The coupler 108 can be engaged with the articular body 104 in a second engaged configuration that prevents relative rotation and inadvertent disengagement once an amount of eccentricity (or no eccentricity) is selected. The second configuration can be provided by applying an impaction force to the articular body 104 while holding the coupler 108 generally stationary. The clearances distances 226, 228 are each generally greater in the first engaged configuration than in the second engaged configuration due to the impaction force. The lesser (but non-zero) clearance distances 226, 228 in the second engaged configuration can ensure that the coupler 108 and the articular body 104 can be coupled by an interference fit, such as a Morse taper.

FIG. 4 shows that the lateral side 222 of the articular body 104 can have indicia 240A for aiding in positioning the articular body 104 over the coupler 108 along the continuous zone 140. For example, the continuous zone 140 can provide for "+1" "+2" and "+3" to indicate adjustment with progressively more eccentricity. In some embodiments, the indicia 240A corresponds to millimeters of offset (e.g., 1 mm, 2 mm, 3 mm of offset respectively) or can just indicate a progressively greater extent. Because the coupler 108 can be freely moveable along the zone 140, eccentricity adjustment between a 0 mm offset and a 4 mm offset positions and also positions between the indicated positions can be provided, including, but not limited to, such as between +1 and +2, e.g., +1.5.

In some embodiments, the plurality of discrete position sites 160 can include radial notches 244 (or other radially extending edges capable of overlap) that provide for discrete eccentricity adjustments. In some embodiments, the radial notches 244 are configured to receive the protrusion 234 of the collar 230. The profile, outline, edges, or shapes of the radial notches 244 can match or invert that of the protrusion 234 such as to provide a fixed position. In one embodiment, the notch 244 can be a negative of the protrusion 234, e.g., the notch 224 can be concave where the protrusion 234 is convex. The concave notch 244 can have a portion that is radially inward of a radially outer portion of the protrusion 234. See FIG. 4A and the corresponding description thereof. The protrusion 234 can be inserted axially into one of the notches 244 in the illustrated embodiment. The matching or inverted configurations, e.g., outline, edges, or shapes, of the protrusion 234 and the notches 244 prevented relative rotation between the coupler 108 and the articular body 104 when the protrusion 234 is engaged with the notch 244. For example, as shown in FIG. 4 an opposing side 231 of the collar 230 disposed away from the protrusion 234 is closely adjacent to or in contact with an inner wall of the first recess 220 (adjacent to the +4 indicia) when the protrusion 234 is in the notch 244 at the +0 indicia. This contact or close adjacency and/or the shape of the notch 244 prevent or prevents the rotation of the coupler 108 within the body 104 unless the coupler 108, and therefore the protrusion 234, is retracted axially away from the body 140 until the protrusion 234 is spaced away from the surface 222. Thus, the coupler 108 is at least radially secured to the articular body 104 when any one of the notches 244 receives the protrusion 234. This condition is referred to above as a first engaged configuration. In other embodiments, a radially oriented detent can be provided between the articular body 104 and the coupler 108. The radial notches 244 of the discrete position site 160 provides for discrete (e.g., "+0", "+1", "+2", "+3", and "+4") eccentricity adjustments. The discrete positions corresponding to the sites 160 can be indicated by indicia 240B. In some embodiments, the markings of the indicia 240B corresponds to millimeters of offset (e.g., 0 mm, 1 mm, 2 mm, 3 mm, and 4 mm of offset respectively). In contrast to the continuous zone 140, the discrete position site 160 provides for adjustments of eccentricity at specific, fixed increments and do not allow for intermediate position, e.g., +1.5.

In one embodiment, one or more radial notches 244 is provided without enclosing the protrusion 234 on both. For example, the notch 244 can provide a radially extending edge that provides a positive stop at one or both ends of the continuous zone 140. In such embodiment, a position such as +0 or +4 can be confirmed by rotating the protrusion 234 into direct circumferential contact with such a notch. For example, in FIG. 4A the circumferential edge 237 extends between two radially inward portions. One of these two portions could be eliminated such that a stop is provided at an end of one or more of continuous zones of eccentricity adjustment. This configuration is elaborated upon in FIG. 12A and in the description thereof.

Figure 7:
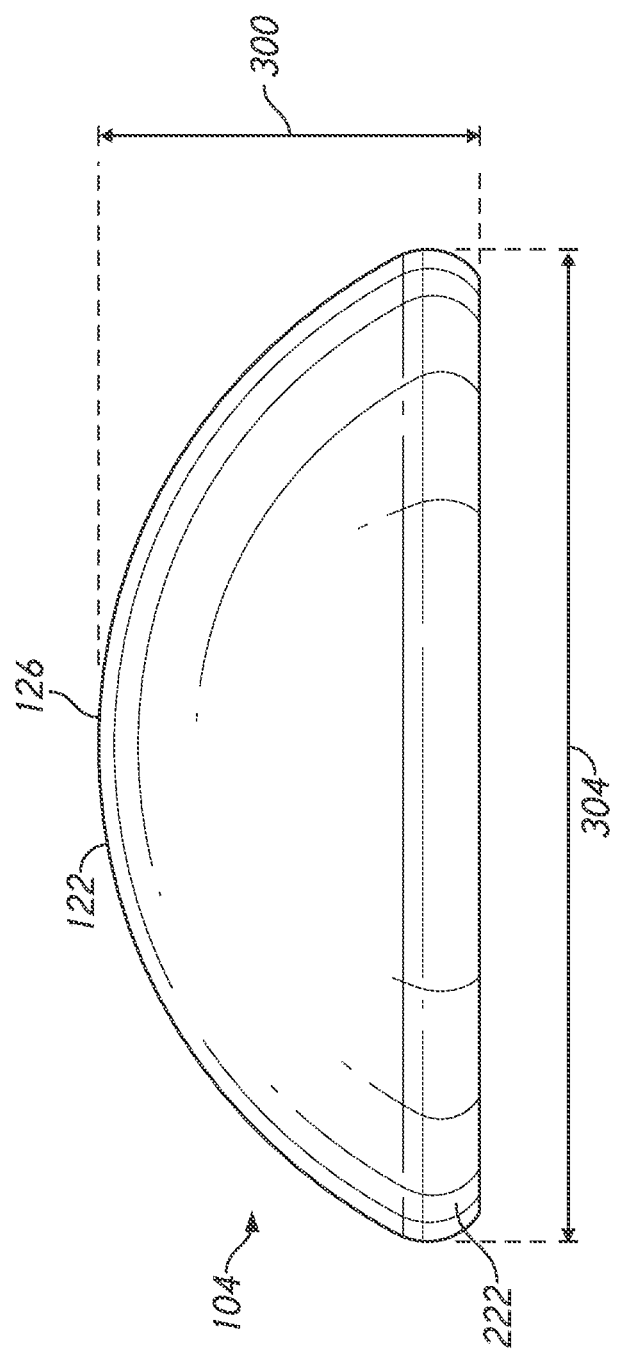
FIG. 7 is a side view of an articular body that can be used in the humeral head assembly of FIG. 2.

FIG. 7-8B illustrate the articular body 104 in greater detail. As discussed above, one side of the articular body 104 includes the articular surface 126. In this embodiment, the articular surface is convex, which presents an anatomical configuration. The articular body 104 has a height 300 and a width 304 that are configured to provide good fit in the shoulder joint space. In some examples, the height 300 of the articular body 104 can be between about 10 mm and about 30 mm, between about 13 mm, and about 27 mm. In some embodiments, the height of the articular body 104 can be about 13.0 mm, about 16.0 mm, about 18.0 mm, about 19.0 mm, about 27.0 mm, etc. The articular body 104 can be made of a variety of materials, such as CoCr, titanium, pyrocarbon, or other advantageous articular material and can include a solid or layered structure.

FIG. 8A illustrates further details of the coupling portion 128. As discussed above, the coupling portion 128 includes the first recess 220 in the lateral side 222. The first recess 220 is configured to receive the first portion 200 and the collar 230 of the coupler 108. In some embodiments, the first recess 220 of the coupling portion 128 is offset from the center 122 of the articular body 104. The first recess 220 coupling portion 128 can have an offset of between about 1.95 mm and about 2.05 mm, or can be about 1.95 mm, or about 2.00 mm, or about 2.05 mm from the center 122 of the articular body 104. FIG. 8B shows that in one example, a longitudinal axis 320 of the second recess 224 intersecting the end 225 thereof and extending perpendicular to a plane of the lateral side 222 is offset from the center 122 of the articular surface 126 in this manner or by these amounts.

In the embodiment shown in FIG. 8A, the continuous zone 140 forms an opening configured to accommodate the collar 230 and, for example, the protrusion 234 of the collar 230 through a range of eccentricity adjustments. The coupling portion 128 can include the indicia 240A indicating the amount of eccentricity provided when the protrusion 234 is directed toward any of the various positions along the continuous zone 140 of the coupling portion 128. For example, the coupling portion 128 in FIG. 8A indicates that the articular body 104 can be rotated along the continuous zone 140 to provide between 0 mm-1 mm of eccentricity adjustment (between the "+0" and "+1" indicia 240A); between and including 1 mm-2 mm of eccentricity adjustment (between the "+1" and "+2" indicia 240A); between and including 2 mm-3 mm of eccentricity adjustment (between the "+2" and "+3" indicia 240A); and between 3 mm-4 mm of eccentricity adjustment (between the "+3" and "+4" indicia 240A). In some embodiments, the continuous zone 140 can span an angle α4, providing about 122°4' of movement. In the illustrated embodiments, eccentricity adjustment results from providing relative rotation between the articular body 104 and the coupler 108. If the coupler 108 is disposed in a humeral, glenoid, scapular, femoral, or tibial anchor on the surface S of the humerus H, glenoid, scapula, femur, or tibia, and is held stationary, rotation of the articular body 104 causes the center 122 of the articular surface 126 of the articular body to move across the surface S. Thus, if the centered configuration 120 is initially provided in the situation illustrated in FIG. 1B, the surgeon can provide eccentricity adjustment by rotating the articular body 104 through a selected degree of rotation to move the center 122 of the articular surface 126 toward the center 48 of the surface S. Thus, the offset illustrated in FIG. 1B can be addressed with the second configuration 124 following some degree of eccentricity adjustment. In some embodiments, the continuous zone 140 can provide at least 90 degrees of eccentricity adjustment. In some examples, the continuous zone 140 can provide from about 90 to about 180 degrees of eccentricity adjustment.

In the embodiment shown in FIG. 8A, each of the discrete position sites 160 is located at a corresponding radial notch 244 configured to receive the protrusion 234 of the collar 230. In some embodiments, at least one of the radial notches 244 is disposed circumferentially adjacent to the continuous zone of eccentricity adjustment. Each of the radial notches 244 can prevent rotation of the articular body 104 relative to the coupler 108, as discussed above, in an engaged configuration. The discrete position sites 160 correspond to indicia 240B indicating the amount of eccentricity provided at each of the discrete position sites 160. For example, the coupling portion 128 in FIG. 8A indicates that the humeral head assembly 100 can be rotated to each of the discrete position sites 160 to provide 0 mm of eccentricity adjustment (at the "+0" indicia 240B); 1 mm of eccentricity adjustment (at the "+1" indicia 240B); 2 mm of eccentricity adjustment (at the "+2" indicia 240B); 3 mm of eccentricity adjustment (at the "+3" indicia 240B); and 4 mm of eccentricity adjustment (at the "+4" indicia 240B). In some embodiments, the position of no eccentricity (e.g. "+0" indicia 240B) is 180 degrees rotationally offset from the position of maximum eccentricity (e.g. "+4" indicia 240B).

In some embodiments, the coupling portion 128 is composed entirely of a continuous zone 140. In some examples, the coupling portion 128 is composed entirely of a continuous zone 140 with a single discrete position site 160, such as at a position corresponding to the centered configuration 120, e.g. at the "+0" radial notch 244 if such embodiment includes discrete position indicia 240B.

In some embodiments, the angle α1 between the "+0" radial notch 244 and the "+1" radial notch 244 is at or about 28°58'. In some embodiments, the angle α2 between the "+0" radial notch 244 and the "+2" radial notch 244 is at or about 60°. In some embodiments, the angle α3 between the "+0" radial notch 244 and the "+3" radial notch 244 is at or about 97°11'. In some embodiments, the angle α3 between the "+0" radial notch 244 and the "+4" radial notch 244 is at or about 180°.

FIG. 8A illustrates an eccentricity adjustment between the ranges of 0 mm-4 mm that can be achieved by engaging the coupler 108 with the continuous zone 140 of eccentricity adjustment or with the at least one discrete position site 160 for eccentricity adjustment. The continuous zone 140 can provide eccentricity adjustment through all values in the range of 0 mm-4 mm of eccentricity adjustment while the at least one discrete position site 160 provides precise eccentricity adjustment at pre-determined values (e.g. 0 mm, 1 mm, 2 mm, 3 mm, and 4 mm). In some embodiments, the coupling portion 128 is configured to allow a surgeon to adjust the articular body 104 in a clockwise or a counter-clockwise direction to achieve the desired eccentricity adjustment. This aspect can provide ease of use for the surgeon as the articular body 104 can engage the coupler 108 at any orientation.

FIG. 8B illustrates the first recess 220 and the second recess 224 extending into the articular body 104. The first recess 220 can have a height 220h of between about 2.669 mm and about 2.769 mm, or about 2.669 mm, about 2.719 mm, or about 2.769 mm, etc. As discussed above, the first recess 220 can be formed in or from the lateral side 222 and can form part of the coupling portion 128 in the articular body 104.

The second recess 224 can extend from the first recess 220 into the articular body 104. In some embodiments, the second recess 224 can have a height 224h of about 8.60 mm. In some embodiments, the second recess 224 can have a tapered profile such that the diameter 224d of the second recess 224 decreases as the second recess 224 extends into the articular body 104. The diameter 224d can have a diameter that ranges from about 9.195 mm to about 9.235 mm. The second recess 224 can be configured to engage with the first portion 200 of the coupler 108 in a Morse taper or other form of interference fit. The tapered walls of the second recess 224 can allow the first portion 200 of the coupler 108 to be secured within the articular body 104 such that there is no relative movement between the articular body 104 and the coupler 108, e.g., between the collar 230 and the lateral side 222. In some embodiments, a longitudinal axis 320 of the second recess 224 can be offset from the center 122 of the articular surface 126. In some embodiments the offset is disposed between a longitudinal axis 320 of the second recess 224 and the center 122 of the articular surface 126.

Figure 9:
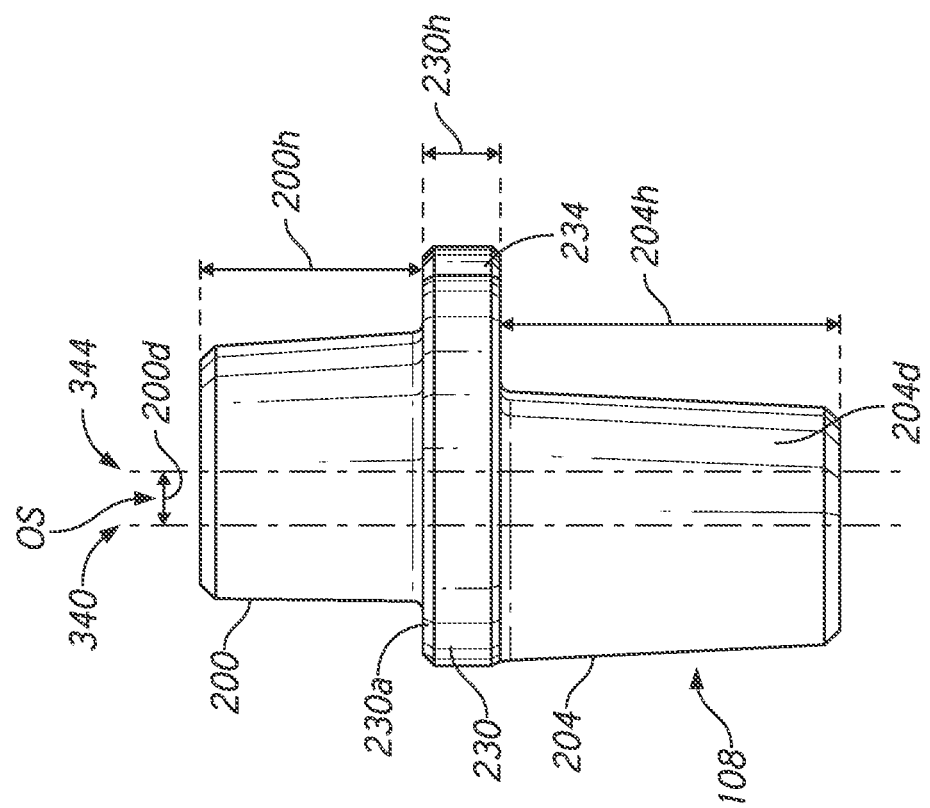
FIG. 9 is a side view of a coupler of the humeral head assembly of FIG. 2.
Figure 11:
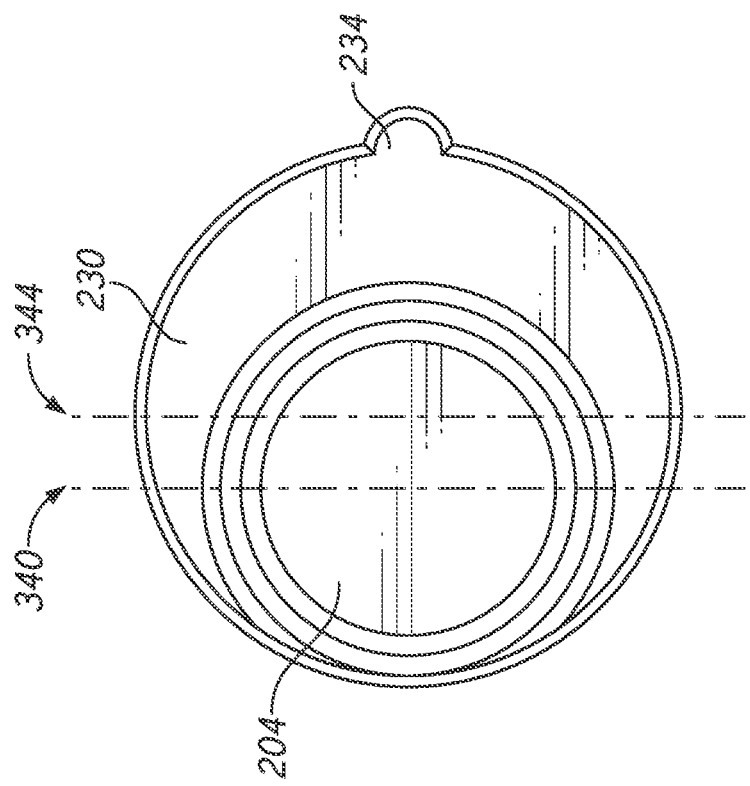
FIG. 11 is a lateral side view of the coupler of FIG. 9.
Figure 10:
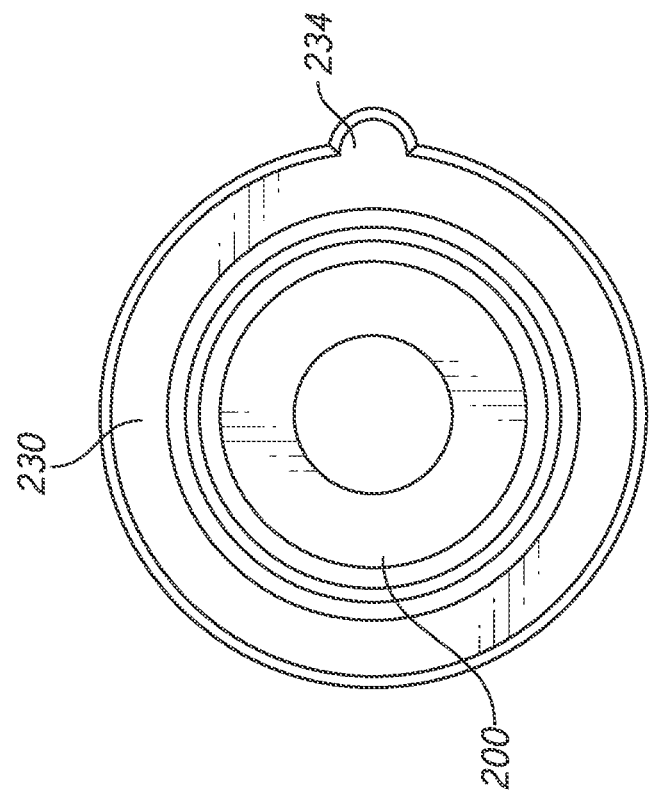
FIG. 10 is a medial side view of the coupler of FIG. 9.

FIGS. 9-11 illustrate various view of an embodiment of the coupler 108. The first portion 200 of the coupler 108 can be configured to engage the articular body 104. In some examples, the first portion 200 can have a height 200h of between about 7.90 mm and about 8.10 mm, or about 7.90, 8.00 mm, or about 8.10 mm. In some embodiments, the first portion 200 can have a diameter 200d at a free end thereof of between 9.205 mm and about 9.235 mm, or about 9.205 mm, about 9.220 mm, about 9.235 mm, etc. In some examples, the diameter 200d of the free end of the first portion 200 is greater than the diameter 224d of the second recess 224 at the end 225 but smaller than the diameter of the recess 224 at the surface 223 such that the first portion 200 can be received and secured within the second recess 224.

The second portion 204 can be configured to mate with another member of a joint prosthesis (e.g. a coupling feature 44 disposed at a surface S of the humerus H, glenoid, scapula, femur, or tibia). In some examples, the second portion 204 can have a height 204h of between about 11.90 mm and about 12.10 mm, or at about 11.90 mm, about 12.00 mm, or about 12.10 mm. In some embodiments, the second portion 204 can have a diameter 204d of between about 9.205 mm and about 9.235 mm, or about 9.205 mm, about 9.220 mm, or about 9.235 mm, etc. In some examples, the diameter 204d can change over its length and range from about 9.205 mm to about 9.235 mm.

The coupler 108 can include the collar 230 at the distal end of the first portion 200. The collar 230 can be configured to fit within the first recess 220 of the articular body 104. In some examples, the collar 230 can have a height of between about 2.45 mm and about 2.55 mm, or at about 2.45 mm, about 2.50 mm, or about 2.55 mm. In some examples, the collar 230 can include the protrusion 234, which as discussed above, is configured to be retained within one of the radial notches 244 of the at least one discrete position sites 160 or to be disposed within or along the continuous range 140.

In some examples, the coupler 108 is asymmetrical such that the second portion 204 had a different longitudinal axis 340 than a longitudinal axis 344 of the first portion 200. The longitudinal axis 340 can be aligned with the center 122 of the articular body 104 (e.g., when the protrusion 234 is aligned with the +0 site 160). When so aligned, the assembly 100 will provide a non-eccentric arrangement as in FIG. 1A. The longitudinal axis 340 can be offset from the center 122 of the articular body 104 (e.g., when the protrusion 234 is not aligned with the +0 site 160). When so offset, the assembly 100 will provide an eccentric arrangement as in FIG. 1B. As illustrated in FIGS. 9-11, the distance between the longitudinal axis 340 of the second portion 204 and the longitudinal axis 344 of the first portion 200 forms an offset OS. In some embodiments, the offset OS can range between about 1.95 mm and about 2.05 mm, or can be about 1.95 mm, or about 2.00 mm, or about 2.05 mm.

In some embodiments, when the coupler 108 is engaged with the articular body 104, the first portion 200 of the coupler 108 aligns with the longitudinal axis 320 of the second recess 224. As discussed above and shown in FIG. 8B, the longitudinal axis 320 of the second recess 224 is offset from the center 122 of the articular surface 124. In some examples, as the coupler 108 is asymmetrical, the longitudinal axis 340 of the second portion 204 may or may not align with the center 122 of the articular surface 124 depending on the arrangement of the humeral head assembly 100. As discussed above in connection with FIGS. 2 and 4-5A, when the humeral head assembly 100 is in the centered configuration 120, the center 122 of the articular surface 124 can be co-linear with the longitudinal axis 340 of the second portion 204. In contrast, when the humeral head assembly 100 is in the eccentric configuration 124 as shown in FIG. 6, the longitudinal axis 340 of the second portion 204 is offset from the center 122 of the articular surface 124. The foregoing shows that the humeral head assembly 100 can provide the configuration of FIG. 1A and a range of eccentric configurations including that of FIG. 1B and thus is a very adaptable assembly and further is able to reduce the complexity of surgical kits and any unused components thereof.

B. Humeral Head With A Plurality of Continuous Adjustment Zones

Figure 12:
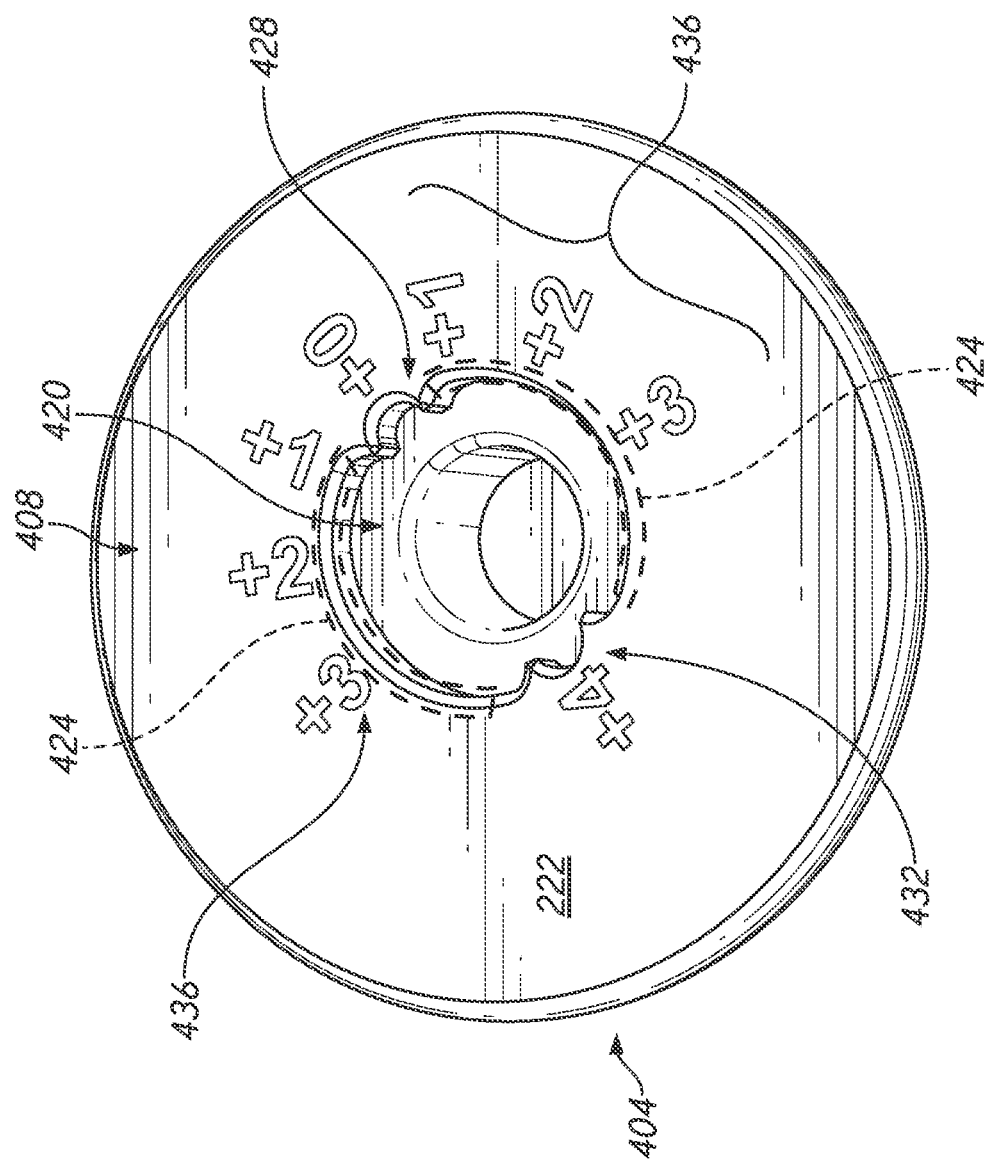
FIGS. 12 and 12A are lateral side views of further embodiments of an articular body suitable for another embodiment of a humeral head assembly.
Figure 12A:
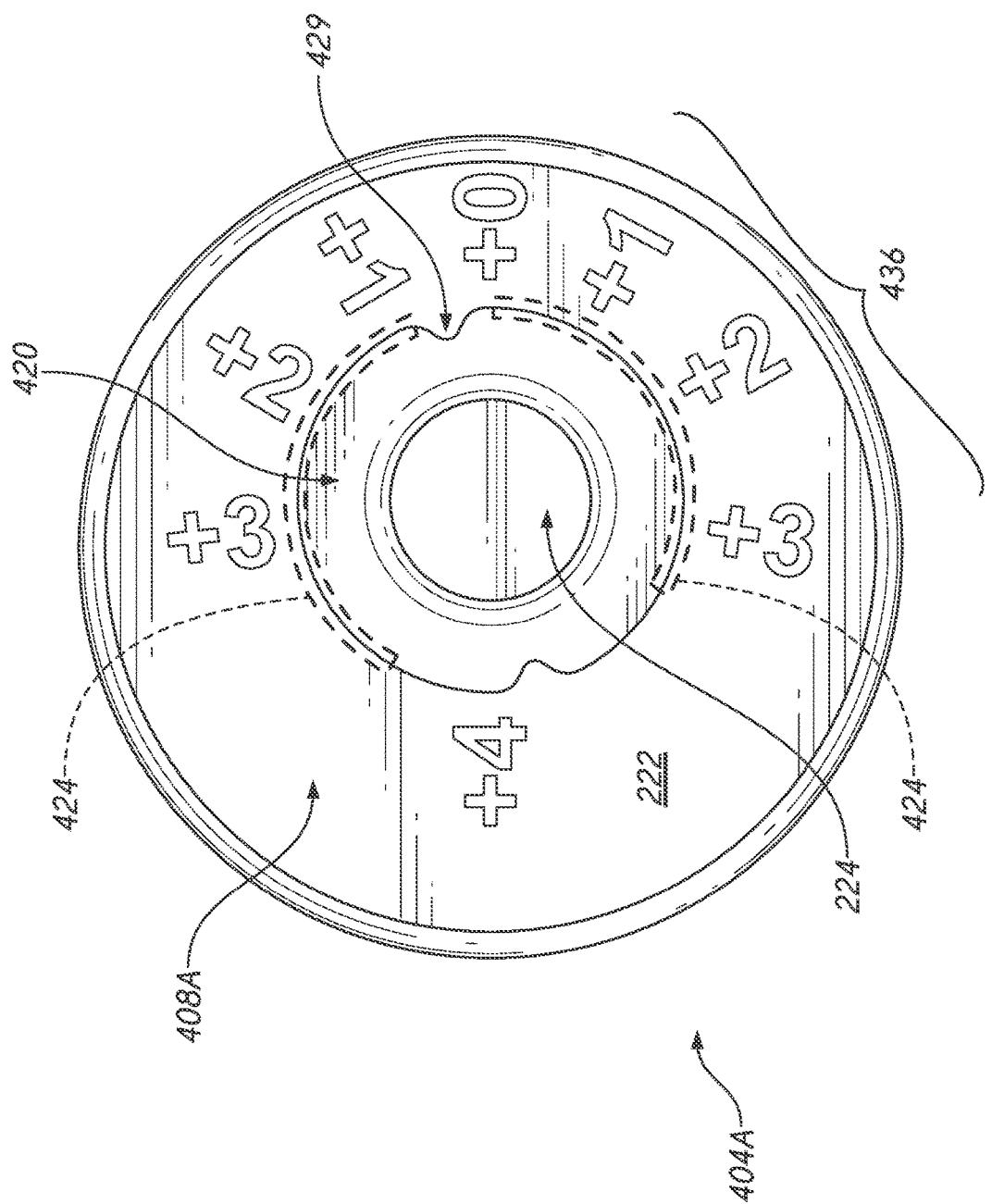

FIGS. 12 and 12A illustrate other embodiments of articular bodies 404, 404A that can form part of a humeral head assembly similar to the humeral head assembly 100. The discussions of the articular body 104 and the humeral head assembly 100 set forth above that are relevant to the discussion of the articular body 404 and to the articular body 404A will not be repeated, but one skilled in the art will understand that such discussions shall supplement the following discussion of the articular body 404.

The articular body 404 has a coupling portion 408, as illustrated in FIG. 12. The coupling portion 408 forms a first recess 420 in the articular body 404. The coupling portion 408 can include a plurality of continuous zones 424 (denoted by shaded regions). The continuous zones 424 can be separated by one or more discrete position sites 428. As with the coupling portion 128, each of the discrete position sites 428 can include a radial notch 432. In some embodiments, the continuous zone 424 of eccentricity adjustment and the one or more discrete position sites 428 are disposed in a same plane, e.g., in a plane parallel to the lateral side 222, located between the side 222 and the articular surface (not shown but located opposite the side 222). In some examples, the continuous zone 424 of eccentricity adjustment is located between discrete eccentricity positions (e.g., discrete position sites 428).

The coupling portion 408 can be configured to engage with the collar 230 of the coupler 108. The plurality of continuous zones 424 form an opening configured to accommodate the collar 230 and, for example, the protrusion 234 of the collar 230 through a range of eccentricity adjustments. The coupling portion 408 can include a plurality of indicia 436 indicating the amount of eccentricity provided at various positions along the continuous zones 424. In the coupling portion 408, the articular body 404 can be rotated in either direction to engage with one of the continuous zones 424 to provide between 0 mm-1 mm of eccentricity adjustment (between the "+0" and "+1" indicia 436); between and including 1 mm-2 mm of eccentricity adjustment (between the "+1" and "+2" indicia 436); between and including 2 mm-3 mm of eccentricity adjustment (between the "+2" and "+3" indicia 436); and between 3 mm-4 mm of eccentricity adjustment (between the "+3" and "+4" indicia 436). In some embodiments, either one of the continuous zones 424 can provide at least 90 degrees of eccentricity. In some examples, either one of the continuous zones 424 can provide from about 90 to about 180 degrees of eccentricity.

In some embodiments, the continuous zones 424 of the plurality of continuous zones are symmetrical. In some embodiments, the continuous zones 424 of the plurality of continuous zone are asymmetrical.

The embodiment of the coupling portion 408 can include two discrete position sites 428 on opposite sides of the coupling portion 408. Each of the discrete position sites 428 form radial notches 432 that are configured to receive the protrusion 234 of the collar 230. In some embodiments, at least one of the radial notches 432 is disposed circumferentially adjacent to the continuous zone of eccentricity adjustment. As discussed above, each of the radial notches 432 can prevent rotation of the articular body 404 relative to the coupler 108. To move from one of the notches 432 to another of the notches or from one of the notches 432 to one of the continuous zones 424, the coupler 108 must be axially disengaged from the articular body 404 such that at least the collar 230 is removed from the first recess 420. In other embodiments, a detent structure can provide mechanical feedback to the user to indicate engagement in a discrete location, e.g., within any of the radial notches 432. Like the continuous zone 424, each of the discrete position sites 428 can include indicia 436 indicating the amount of eccentricity provided at each of the discrete position sites 428. In the embodiment illustrated in FIG. 12, the coupling portion 408 includes two discrete position sites 428—at 0 mm of eccentricity adjustment (at the "+0" indicia 436) and at the 4 mm of eccentricity adjustment (at the "+4" indicia 436). In some embodiments, the position of no eccentricity (e.g. "+0" indicia 436) is 180 degrees rotationally offset from the position of maximum eccentricity (e.g. "+4" indicia 436).

The coupling portion 408 of FIG. 12 differs from the coupling portion 128 in that it includes two continuous zones 424. In this embodiment, a surgeon would be able to confirm through contact with and subsequent engagement in the notches 432 of the discrete position site 360 when the articular body 404 is centered on the coupler 108 and when the articular body 104 is positioned at maximum eccentricity (e.g. 4 mm). Between those ranges, the surgeon is able to freely adjust the position of the articular body 404 about the coupler 108.

FIG. 12A shows further details of the articular body 404A. As discussed the articular body 404A is similar to the articular body 404 except as described differently below. The discussion of the articular body 404 and the other articular bodies are intended to supplement the following discussion and will not be repeated. The articular body 404A includes a coupling portion 408A. The coupling portion 408A includes a first recess 420 and a second recess 224 can extend from the first recess 420. The first recess 420 can be bounded by a plurality of zones or wall segments. The first recess 420 can be bounded by one or a plurality of continuous zones 424. One or both of the continuous zones 424 can extend to an end formed by a stop 429. FIG. 12A shows that a stop 429 can be provided at each end of a first continuous zone 424. The stops 429 can include curved protrusions that extend to peaks disposed into the first recess 420. The peaks of the stops 429 can extend about one-quarter of the width of the first recess 420 from the continuous zones 424 toward the second recess 224. In the illustrated embodiment two continuous zones 424 are provided on opposite sides of the second recess 224.

The continuous zones 424 can be symmetrical about a line intersecting the stops 429, e.g., connecting the peaks of the stops 429. In some embodiments the coupling portion 408A of the articular body 404A is not symmetrical such that the indicia 436 are not spaced apart by the same amount. FIG. 12A shows that the indicia 436 disposed in the portion of the lateral side 222 located in a clockwise direction from +0 correspond to providing 0, 1, 2, or 3 mm of offset. More specifically, when the protrusion 234 of the coupler 108 is advanced into the first recess 420 and is aligned with the +0 of the indicia 436 no additional offset is provided. When the protrusion 234 is advanced into the first recess 420 and is aligned with the +1 of the indicia 436 an additional offset of +1 mm is provided. The indicia 436 that are disposed on the portion of the lateral side 222 located in a clockwise direction from +4 correspond to providing a different range of additional offset. The indicia 436 on this portion of the lateral side 222 indicate a range of adjustment from +1 to +4 mm of additional offset.

The stops 429 differ from the radial notches 432 of the discrete position sites 428 in not being able to enclose the protrusion 234 on both sides when the protrusion 234 is aligned with one of the indicia 436 centered on the radial notches 432. Rather, the engagement of the protrusion 234 is made by contacting one side thereof with one side of the stops 429. An advantage of this is that when the coupler 108 is advanced into the first recess 420 and the protrusion 234 is contacting either one of the stops 429 motion away from the offset position provided at this relative position can be accomplished without having to withdraw the collar 230 out of the first recess 420. Immediate relative rotation of the articular body 404A on the coupler 108 can be provided to move from any of the discrete positions to any other position. The engagement of the protrusion 234 with the stops 429 can be easily confirmed in a tactile manner without requiring any rotational alignment of the protrusion 234 with a notch.

One further variation of an assembly can be provided by modifying the coupler 108 such that the collar 230 has a concave periphery that is configured to either receive the stops 429 or if not aligned therewith to be positional along the continuous zones 424 in the first recess 420. This modification would provide that both sides of the stops 429 would be received within the concave recess of the modified coupler 108 such that in this variation movement from the discrete positions defined by the stops 429 to the continuous zones 424 would require retracting the modified collar of the coupler 108 from the first recess 420.

C. Eccentric Adjustment at an Interface Partially Formed on a Humeral Anchor

Figure 13A:
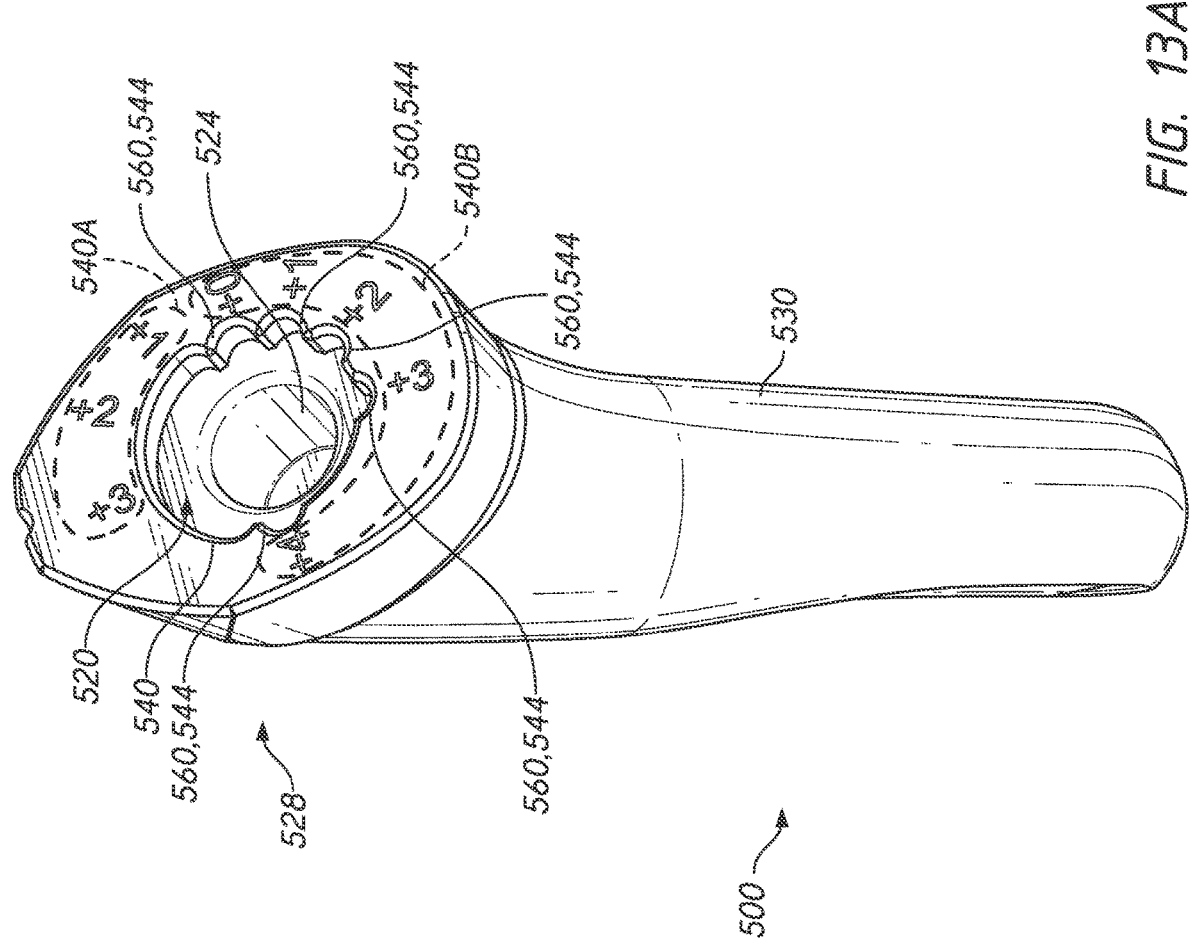
Figure 13B:
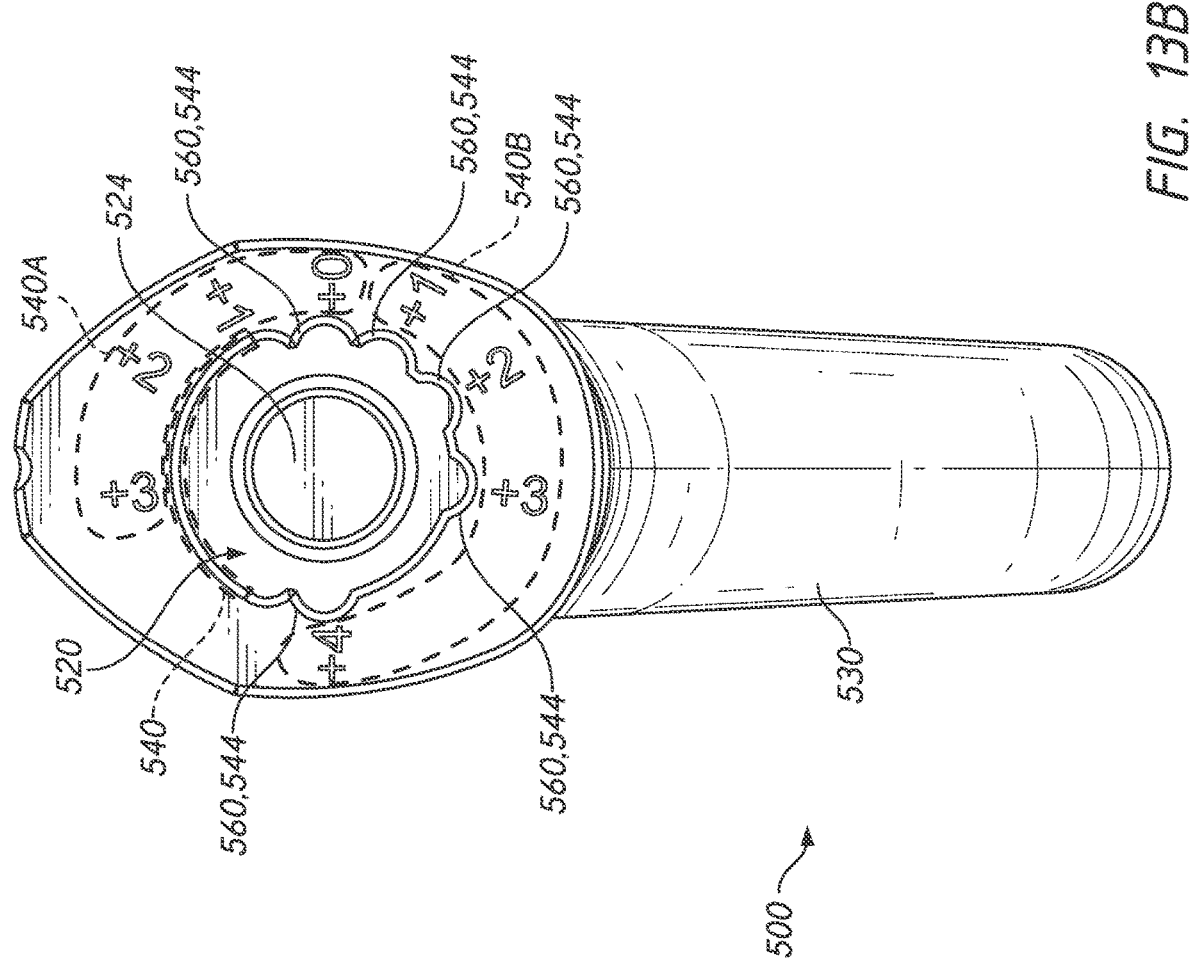

FIGS. 13A-13C illustrate another embodiment of a coupling portion 528. The discussions of the coupling portion 128 set forth above that are relevant to the discussion of the coupling portion 528 will not be repeated, but one skilled in the art will understand that such discussions shall supplement the following discussion of the coupling portion 528.

The coupling portion 528 can be located between the articular surface of an articular body (e.g. articular body 104, articular body 404) and an end of a bone anchor 500. As discussed above, in some embodiments, the coupling portion can be located on a surface of the articular body (e.g. opposite the convex articular surface). In some embodiments, the coupling portion 528 can be located in an end of the bone anchor 500. FIGS. 13A-13C illustrate a bone anchor 500 having a stem 530, but in some embodiments, the bone anchor can be stemless. Examples of stemless bone anchors are found in US2016/0324648 and in U.S. 62/368,036, both of which are hereby incorporated by reference herein in their entireties.

The coupling portion 528 illustrated in FIGS. 13A-13C is similar to the coupling portion 128 of the humeral head assembly 100 disclosed above. However, the coupling portion 408 illustrated in FIG. 12, 12A, or any of the other coupling portions disclosed herein can similarly be located in a surface of the bone anchor 500 (e.g. stem or stemless).

The coupling portion 528 forms a first recess 520 in a medial surface of the stem 530. The coupling portion 528 can include a continuous zone 540 and at least one discrete position site 560 (denoted by a shaded region). The coupling portion 528 can include at least one discrete position site(s) 560. As with the coupling portion 128, each of the discrete position sites 560 can include a radial notch 544 or other radially extending edge configured to radially overlap with a portion of a coupler, as discussed below. In some embodiments, the continuous zone 540 of eccentricity adjustment and the at least one discrete position site 560 are disposed in a same plane, e.g., in a plane lateral to but parallel with the medial surface of the stem 530. In some examples, the continuous zone 540 of eccentricity adjustment is located between discrete eccentricity positions (e.g., discrete position sites 560).

The coupling portion 528 can be configured to engage with a collar 630 of a coupler 608 that can be engaged with the coupling portion 528. The continuous zone 540 forms an opening configured to accommodate the collar 630 and, for example, a protrusion 634 of the collar 630 through a range of eccentricity adjustments. The coupling portion 528 can include a plurality of indicia 540A indicating the amount of eccentricity provided at various positions along the continuous zone 540. The coupler 608 can be rotated in the coupling portion 528 to provide between 0 mm-1 mm of eccentricity adjustment (between the "+0" and "+1" indicia 540A); between and including 1 mm-2 mm of eccentricity adjustment (between the "+1" and "+2" indicia 540A); between and including 2 mm-3 mm of eccentricity adjustment (between the "+2" and "+3" indicia 540A); and between 3 mm-4 mm of eccentricity adjustment (between the "+3" and "+4" indicia 540A). In some embodiments, the continuous zone 540 can provide at least 90 degrees of eccentricity. In some examples, the continuous zone 540 can provide from about 90 to about 180 degrees of eccentricity.

One or more of the plurality of discrete position sites 560 can include radial notches 544 that are configured to receive the protrusion 634 of the collar 630. In some embodiments, at least one of the radial notches 544 is disposed circumferentially adjacent to the continuous zone of eccentricity adjustment. As discussed above, each of the radial notches 544 can prevent rotation of the coupler 608 relative to the coupling portion 528 in the surface of the stem 530. The notches allow for a first engaged configuration in which rotation is prevented but the coupler 608 and the anchor 500 are not secured in an interference fit and can be easily disengaged. To move from one of the radial notches 544 to another of the notches or from one of the radial notches 544 to the continuous zone 540, the coupler 608 can be axially disengaged from (e.g., moved medially relative to) the medial surface of the stem 530 such that at least the collar 630 is removed from the first recess 520. In other embodiments, a portion of a detent structure can be provided to indicate to the user a rotationally engaged configuration. Like the continuous zone 540, each of the discrete position sites 560 can include indicia 540B indicating the amount of eccentricity provided at each of the plurality of discrete position site 560. In the embodiment illustrated in FIGS. 13A-13C, the coupling portion 528 includes four (4) discrete position sites 560—at 0 mm of eccentricity adjustment (at the "+0" indicia 540B), at 1 mm of eccentricity adjustment (at the "+1" indicia 540B), at 2 mm of eccentricity adjustment (at the "+2" indicia 540B), at 3 mm of eccentricity adjustment (at the "+3" indicia 540B), and at the 4 mm of eccentricity adjustment (at the "+4" indicia 540B). In some embodiments, the position of no eccentricity (e.g. "+0" indicia 540A) is 180 degrees rotationally offset from the position of maximum eccentricity (e.g. "+4" indicia 540A).

In some embodiments, the first recess 520 of the coupling portion 528 opens up to a second recess 524. The second recess 524 can have a smaller diameter than the first recess 520. The second recess 524 can be configured to receive a tapered end portion of the coupler 608. The tapered end portion can be similar to the first portion 200 of the coupler 108. In the illustrated embodiment, the tapered end portion is aligned with a center of the second recess 524. A medial end 632 of the coupler 608 projects medially from the collar 630. The medial end 632 of the coupler 608 is configured to engage a recess in an articular body that can be similar to the articular body 104. The longitudinal axis of the medial end 632 of the coupler 608 is offset from the tapered end (and from the center of the second recess 524) such that rotation of the coupler 608 along the continuous zone 540 or to any of the discrete position sites 560 results in adjustment of the extent of eccentricity (if any) to provide for centering of the articular body over the resected surface of the humerus even if the anchor 500 is not centered on the resected surface.

Figure 14B:
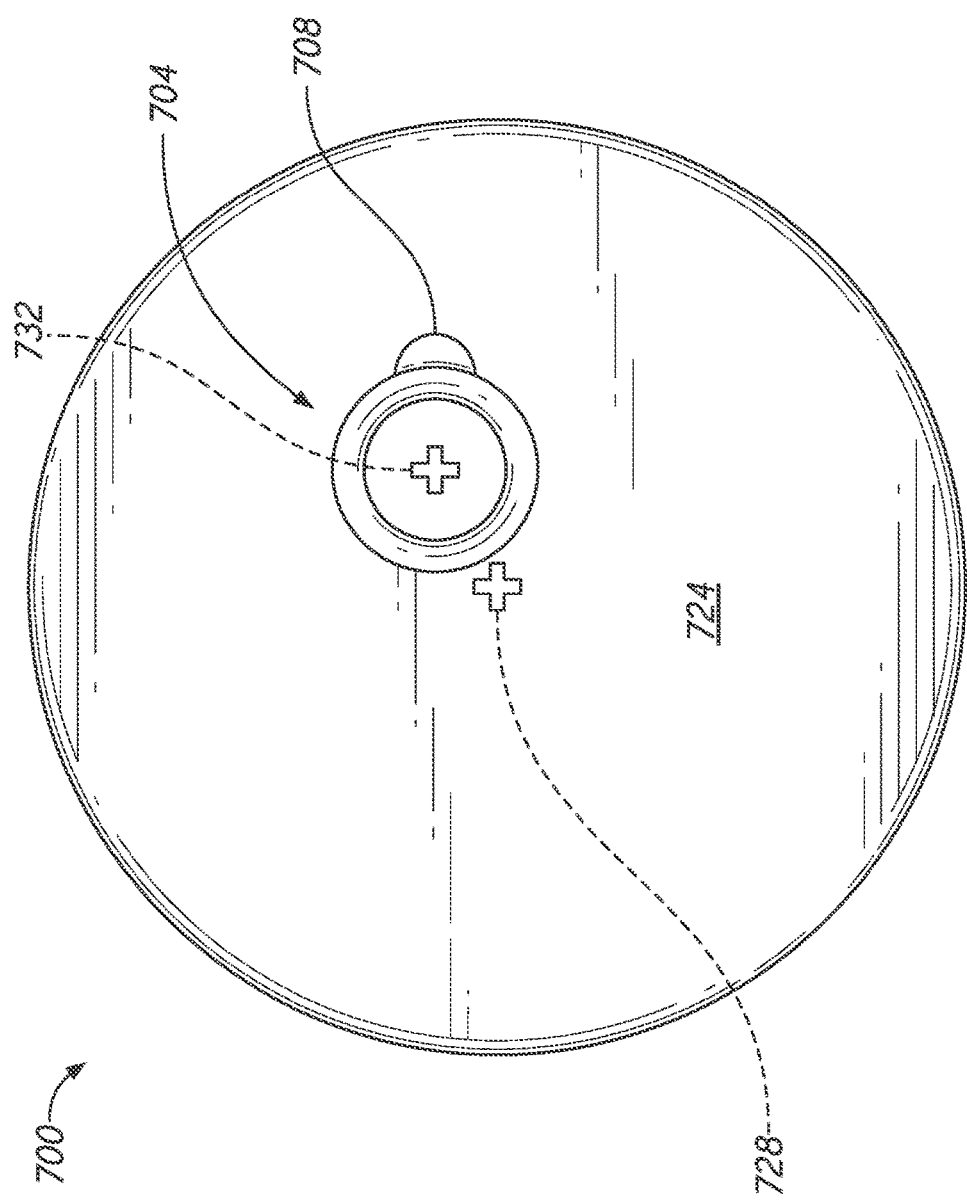
Figure 14C:
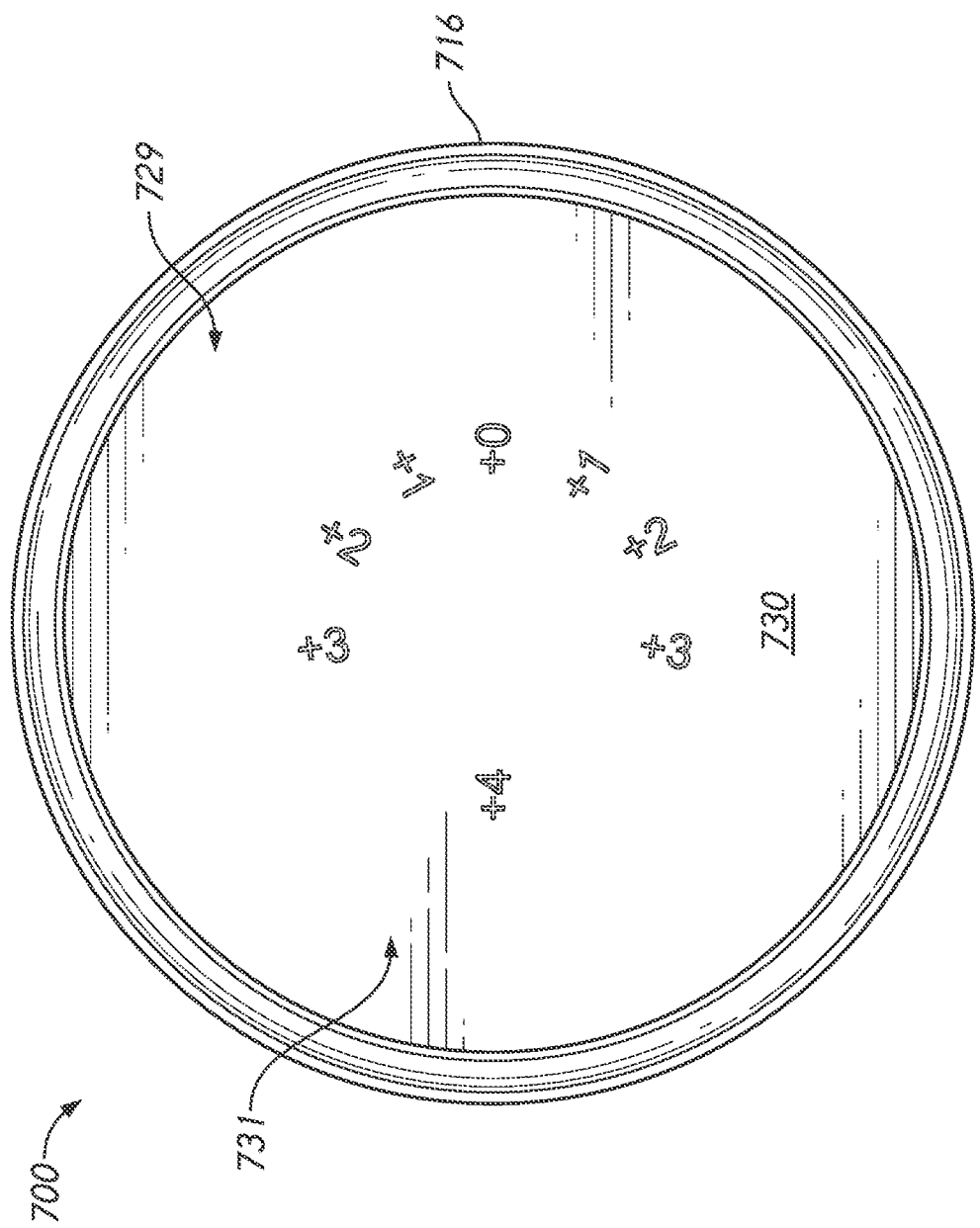

FIGS. 14A-14C show that the foregoing embodiments can also be applied to a reverse shoulder assembly. A reverse shoulder assembly is one in which the natural articular surfaces of the humerus are modified such that a convex articular surface is provided on the scapula and a concave articular surface is provided on the humerus. FIG. 14A show an exploded view of the anchor 500 and a tray 700 of a reverse shoulder assembly. The anchor 500 can have any of the features discussed above. The anchor 500 also can have any combination of continuous and position sites. FIG. 14A shows the notches 544 formed within the first recess 520. The anchor 500 also includes the second recess 524 which extends from the first recess 520 further into the anchor 500.

The tray 700 can have a taper 704 projecting from a humeral facing wall 724 and a recess on the opposite side of the tray 700 from the humeral facing wall 724. The recess can be partly defined by an inner circumference 712 which is surrounded by an inner sidewall 716. The tray 700 can be configured to securely retain an articular body (not shown) which is inserted into the recess in the space surrounded by the inner sidewall 716. The inner sidewall 716 can have one or a plurality of fins 720 disposed about the inner sidewall 716. The fins 720 can be configured to engage an outer sidewall of the articular body to hold the articular body in place in one embodiment. The articular body has a concave articular surface as discussed above.

FIG. 14B shows further details of the tray 700. The tray 700 can be symmetrical, e.g., having a circular outer periphery about the humeral facing wall 724. The tray 700 can have a center 728 from which a radius of the circular periphery can be measured. In various advantageous embodiments the center 728 is disposed offset from a center 732 of the taper 704. The off-set distance between center 728 and the center 732 enables a rotation of the tray 700 relative to the anchor 500 to change the location of the tray 700 (and thereby the articular body coupled therewith) relative to the resected face of the humerus. Thus, even if the anchor 500 is off-set from the center of the humerus the tray 700 can be rotated relative to the anchor 500 to a position in which the center 728 is centered, substantially centered or closer to the of the humerus than the second recess 524 or the taper 704. The tray 700 can include a protrusion 708 that can be aligned to discrete or continuous zones as discussed further below. FIG. 14C shows the opposite side of the tray 700 shown in FIG. 14B. The side shown in FIG. 14C faces the scapula when the tray 700 is implanted and may be referred to as a medial side. The tray 700 includes a wall 730 that is located opposite the humeral facing wall 724. The wall 730 and the inner sidewall 716 at least partially define a concave space 729 in which an articular insert can be disposed. In one embodiment indicia 731 are provided on the medial side, e.g., on the wall 730 to facilitate alignment of the tray 700 relative to the anchor. The indicia 731 on the wall 730 can be aligned with the indicia on the anchor 500 to provide the off-set position indicated. For example, the protrusion 708 can be placed in the +0 position on the anchor 500 and when so placed the +0 mark of the indicia 731 will be aligned with the +0 on the anchor 500. When the tray 700 is rotated such that the +1 mark of the indicia 731 is moved to the horizontal position (where +0 is in FIG. 14C) the surgeon can know that the protrusion 708 is aligned with +1 in the upper (as depicted in FIG. 14A) continuous zone of the anchor 500. When the tray 700 is rotated such that the +2 mark of the indicia 731 is moved to the horizontal position the surgeon can know that the protrusion 708 is aligned with +2 in the upper continuous zone of the anchor 500. When the tray 700 is rotated such that the inverted +1 mark of the indicia 731 is moved to the horizontal position the surgeon can know that the protrusion 708 is aligned with the inverted +1 in the lower portion of the anchor 500. Visual confirmation on the tray 700 may not be required for discrete zones (as in the lower portion of the anchor 500) but still provides a convenient visual confirmation. Also, the anchor 500 can be provided with upper and lower continuous zones, similar to the arrangements of FIGS. 12 and 12A. The indicia 731 thus can give a visual confirmation of the position of the tray 700 relative to the anchor 500. The visual confirmation enables the surgeon to accurately position the tray 700 and also to make a record during the surgery of the position to enhance the patient's medical record.

A method of implanting a humeral assembly including the anchor 500 and the tray 700 can include surgically exposing the humerus at the shoulder. The humerus is then resected to create the exposed surface S (see FIG. 1). The anchor 500 can thereafter be placed in the humerus by creating a space in the cancellous bone of the humerus for a stemmed anchor. If a stemless anchor is used, less or no additional bone preparation may be required. The tray 700 can be used to provide an adjustment of the position of the tray 700 (and an articular body coupled therewith) if following placement the position of anchor 500 it is determined that some adjustment is needed. For example, the tray 700 can be advanced as indicated by arrow A to be coupled with the anchor 500 by advancing the taper 704 into the second recess 524 until the tray 700 comes to rest on the anchor 500. The tray 700 can be rotationally oriented in either direction of the arrow B as the tray 700 is advanced into first recess 520 and the second recess 524. In one technique the protrusion 708 is initially aligned with the +0 position such that no additional offset is provided, e.g., the center 728 is aligned with the center of the second recess 524. If offset is needed the protrusion 708 can be moved along the continuous zone 540 to +1, +2, +3, or any other position therebetween. The protrusion 708 can be moved to any one of the notch 544, e.g., to the +1, +2, +3, or +4 positions. The position can be visually confirmed by reference to the indicia 731 as discussed above. Once alignment is confirmed the tray 700 can be secured to the anchor 500 by engaging the taper 704 with the walls of the second recess 524, e.g., in a Morse taper connection. The method can include selecting between two continuous zones of adjustment in some embodiments of the anchor 500. After the tray 700 is secured to the anchor 500 a reverse articular body can be coupled with the tray 700 within the inner sidewall 716, e.g., by engaging the fins 720.

Although the anchor 500 has been illustrated as configured for implantation in a humerus, the anchor 500 could be adapted for implantation within a glenoid, scapula, femur, or tibia and still provide advantageous positioning of an articular body thereon in a centered or over a range of eccentric positions as discussed herein.

III. Methods of Assembling the Centered and Eccentric Humeral Head Assembly

The humeral head assembly 100 described allows a surgeon to treat a wider variety of patient anatomy with a kit including fewer components. The articular body 104 and the coupler 108 are adjustable relative to each other such that the humeral head assembly 100 can be used in the centered configuration 120 or the eccentric configuration 124. Although the method below is discussed in connection with the humerus, as discussed herein the assembly 100 and the bone anchor 500 and the coupler 608 can be deployed in other orthopedic applications such as in implanting a glenosphere in a glenoid, a femoral articular body on an end of a femur (e.g., for hip or knee procedures) or for implanting a tibial articular body at an end of a tibia for a joint procedure.

The method of assembling the humeral head assembly 100 can include engaging a first end (e.g. the first portion 200) with the coupler 108 of the articular body 104. The method can then include providing relative rotation between the articular body 104 about the first end (e.g., the first portion 200) of the coupler 108. The relative motion can be along a continuous zone 140 of rotational positions while the first end (e.g., the first portion 200) is partially inserted into the coupling portion 128. As well, the method can include providing relative rotation to align the coupler 108 with a discrete position site 160.

The method of assembling the humeral head assembly 100 can include selecting an amount of eccentricity corresponding to a position within the continuous zone 140 of rotational position or to the at least one discrete position site 160. As described with regard to FIGS. 3, 8A, 12, and 13C, the continuous zone 140, 540 and the at least one discrete position site 160, 560 allow the surgeon to select the amount of eccentricity adjustment required by adjusting the position of the collar 230 within the articular body 104 or by adjusting the position of the collar 530 within the anchor 500.

The method of assembling the humeral head assembly 100 can include securing the articular body 104 about the first end (e.g. first portion 200) of the coupler 108 at the selected amount of eccentricity within the continuous zone 140 or the at least one discrete position site 160. The method of assembling the humeral head assembly including the anchor 500 can include securing the coupler 608 within the anchor 500 about the tapered end of the coupler 608 at the selected amount of eccentricity within the continuous zone 540 or the at least one discrete position site 560. As described above in FIG. 8A-8B, the second recess 224 can be configured to receive the first portion 200. As the walls of the second recess 224 are tapered and gradually reduce in diameter, the second recess 224 can be press-fit or interference fit, e.g., with a Morse taper, about the first portion 200 to secure the articular body 104 to the coupler 108 to prevent relative movement between the articular body 104 and the coupler 108. Similarly the second recess 524 can be tapered to receive the tapered end portion of the coupler 608 resulting in a Morse taper connection.

In some embodiments, the method of assembling the humeral head assembly 100 includes aligning the alignment feature (e.g. the protrusions 234, 634) of the collars 230, 638) with an eccentricity amount indicia 240A, 240B, 540A, 540B disposed on or adjacent to the coupling portion 128, 538 of the articular body 104 or of the anchor 500.

In some embodiments, the method of assembling the humeral head assembly 100 can also include positioning the protrusion 234 of the collar 230 (or protrusion 634) within a radial notch 244 (or notch 544) of one of the discrete position sites 160 (560). This can also be configured to prevent relative rotation of the coupler 108 with the articular body 104 (or of the coupler 608 with the anchor 500).

The apparatuses and methods herein can enable either of the situations illustrated in FIGS. 1A and 1B to be treated using only one articular body 104 and only one coupler 108 coupled with a bone anchor or with one anchor 500, one coupler 608 and an articular body. In the past, commercial systems provided kits with multiple articular body/coupler combinations that were pre-assembled. Thus, the present application enables a wide range of patients to be treated with fewer components, simpler systems, and less cost.

Terminology

Although certain embodiments have been described herein, the implants and methods described herein can interchangeably use any articular component, as the context may dictate.

As used herein, the relative terms "proximal" and "distal" shall be defined from the perspective of the implant. Thus, proximal refers to the direction of the articular component and distal refers to the direction of an anchor component, such as a stem of a humeral anchor or a thread or porous surface or other anchoring structure of a stemless anchor when the implant is assembled.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments.

The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. In addition, the articles "a," "an," and "the" as used in this application and the appended claims are to be construed to mean "one or more" or "at least one" unless specified otherwise.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 1" includes "1." Phrases preceded by a term such as "substantially," "generally," and the like include the recited phrase and should be interpreted based on the circumstances (e.g., as much as reasonably possible under the circumstances). For example, "substantially spherical" includes "spherical." Unless stated otherwise, all measurements are at standard conditions including temperature and pressure.

As used herein, a phrase referring to "at least one of" a list of items refers to any combination of those items, including single members. As an example, "at least one of: A, B, or C" is intended to cover: A, B, C, A and B, A and C, B and C, and A, B, and C. Conjunctive language such as the phrase "at least one of X, Y and Z," unless specifically stated otherwise, is otherwise understood with the context as used in general to convey that an item, term, etc. may be at least one of X, Y or Z. Thus, such conjunctive language is not generally intended to imply that certain embodiments require at least one of X, at least one of Y and at least one of Z to each be present.

Although certain embodiments and examples have been described herein, it should be emphasized that many variations and modifications may be made to the humeral head assembly shown and described in the present disclosure, the elements of which are to be understood as being differently combined and/or modified to form still further embodiments or acceptable examples. All such modifications and variations are intended to be included herein within the scope of this disclosure. A wide variety of designs and approaches are possible. No feature, structure, or step disclosed herein is essential or indispensable.

Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Moreover, while illustrative embodiments have been described herein, it will be understood by those skilled in the art that the scope of the inventions extends beyond the specifically disclosed embodiments to any and all embodiments having equivalent elements, modifications, omissions, combinations or sub-combinations of the specific features and aspects of the embodiments (e.g., of aspects across various embodiments), adaptations and/or alterations, and uses of the inventions as would be appreciated by those in the art based on the present disclosure. The limitations in the claims are to be interpreted broadly based on the language employed in the claims and not limited to the examples described in the present specification or during the prosecution of the application, which examples are to be construed as non-exclusive. Further, the actions of the disclosed processes and methods may be modified in any manner, including by reordering actions and/or inserting additional actions and/or deleting actions. It is intended, therefore, that the specification and examples be considered as illustrative only, with a true scope and spirit being indicated by the claims and their full scope of equivalents.

Any methods disclosed herein need not be performed in the order recited. The methods disclosed herein include certain actions taken by a practitioner; however, they can also include any third-party instruction of those actions, either expressly or by implication. For example, actions such as "inserting a humeral stem into a humerus" include "instructing insertion of a humeral head into a humerus."

What is claimed is:

1. A method of assembling an articular component of a prosthetic shoulder joint, the method comprising:
    engaging an end of a coupler of a joint implant with a coupling portion of another component of the joint implant;
    providing relative rotation between the end of the coupler and the coupling portion of the other component of the joint implant along a continuous range of rotational positions while the end is engaged with the coupling portion of the other component of the joint implant;
    selecting an amount of eccentricity corresponding to a position within the continuous range of rotational position; and
    securing the other component of the joint implant to the end of the coupler at the selected amount of eccentricity, wherein
    providing relative rotation between the end of the coupler and the coupling portion of the other component comprises rotating a protrusion at the end of the coupler into engagement with a stop structure.

2. The method of claim 1, wherein the other component comprises an articular body of an anatomic humeral assembly.

3. The method of claim 1, wherein the other component comprises a humeral anchor.

4. The method of claim 3, wherein the coupler comprises a portion of a reverse shoulder assembly.

5. A method of assembling an articular component of a prosthetic shoulder joint, the method comprising:
    engaging a first end of a coupler with a coupling portion of an articular body;
    providing relative rotation between the articular body and the coupler about the first end of the coupler along a continuous range of rotational positions while the first end is engaged with the coupling portion or providing relative rotation to align the coupler with a discrete position feature;
    selecting an amount of eccentricity corresponding to a position within the continuous range of rotational position or to the discrete position feature;
    positioning a protrusion of the coupler along the continuous range, wherein the protrusion is between the first end and a second end of the coupler; and
    securing the articular body about the first end of the coupler at the selected amount of eccentricity or discrete position feature.

6. The method of claim 5, wherein the continuous range provides at least 90 degrees of relative rotation.

7. The method of claim 5, wherein the discrete position feature is a radial notch of the coupling portion.

8. The method of claim 7, wherein the radial notch is disposed circumferentially adjacent to a continuous zone of eccentricity adjustment.

9. The method of claim 5, wherein the discrete position feature is located adjacent to a continuous eccentricity zone.

10. The method of claim 5, further comprising aligning an alignment feature of the coupler with an eccentricity amount indicator disposed on or adjacent to the coupling portion of the articular body.

11. The method of claim 10, wherein aligning the alignment feature with the eccentricity amount indicator further comprises aligning the protrusion of the coupler with one of a plurality of indicia of eccentricity disposed on the articular body.

12. The method of claim 5, wherein the coupling portion further comprises a plurality of discrete position features, and wherein providing relative rotation to align the coupler with a discrete position feature comprises selecting between a discrete position of no eccentricity and a discrete position of eccentricity.

13. The method of claim 5, wherein the coupling portion comprises a plurality of discrete position features, each of the discrete position features providing a different amount of eccentricity, and wherein
    providing relative rotation to align the coupler with one of the plurality of discrete position features comprises selecting between a first one of the plurality of discrete position features corresponding to lesser eccentricity and a second one of the plurality of discrete position features corresponding to greater eccentricity.

* * * * *